United States Patent [19]
Braunlich et al.

[11] Patent Number: 5,565,488
[45] Date of Patent: Oct. 15, 1996

[54] OXALYLAMINO-BENZOFURAN- AND BENZOTHIENYL-DERIVATIVES

[75] Inventors: Gabriele Bräunlich, Wuppertal; Rüdiger Fischer, Köln; Mazen Es-Sayed, Wuppertal; Rudolf Hanko, Düsseldorf, all of Germany; Stephen Tudhope, Windsor, Great Britain; Graham Sturton, Bray Maidenhead, Great Britain; Trevor Abram, Marlow, Great Britain; Wendy J. McDonald-Gibson, Wallingford, Great Britain; Mary F. Fitzgerald, Begbroke, Great Britain

[73] Assignee: Bayer Aktiengesellschaft, Leverkusen, Germany

[21] Appl. No.: 448,212

[22] Filed: May 23, 1995

[30] Foreign Application Priority Data

May 31, 1994 [GB] United Kingdom ............... 9410863
May 31, 1994 [GB] United Kingdom ............... 9410891

[51] Int. Cl.$^6$ .................... A61K 31/34; C07D 307/80
[52] U.S. Cl. .................... 514/469; 514/443; 514/470; 546/328; 548/159; 548/311.4; 549/51; 549/55; 549/57; 549/229; 549/293; 549/320; 549/466; 549/468

[58] Field of Search ................... 549/51, 55, 57, 549/466, 468; 514/443, 469, 470

[56] References Cited

U.S. PATENT DOCUMENTS 5,120,742  6/1992  Rasmusson et al. ............... 514/284

FOREIGN PATENT DOCUMENTS 0146243  10/1984  European Pat. Off. .
0551662   7/1993  European Pat. Off. .
0623607  11/1994  European Pat. Off. .

OTHER PUBLICATIONS

S. Nagata et al., Int. Arch. Allergy Immonol., vol. 97, pp. 194–199, (1992).

*Primary Examiner*—Bernard Dentz
*Attorney, Agent, or Firm*—Sprung Horn Kramer & Woods

[57] ABSTRACT

The inventive Oxalylamino-benzofuran- and benzothienyl-derivatives are prepared by reacting the appropriate amino substituted benzofuranes and benzothiophenes with oxalic acid derivatives. The inventive compounds are suitable for the prevention and treatment of acute and chronic inflammatory processes, particularly of the airways.

12 Claims, No Drawings

OXALYLAMINO-BENZOFURAN- AND BENZOTHIENYL-DERIVATIVES

The invention relates to Oxalylamino-benzofuran- and benzothienyl-derivatives, processes for their preparation and their use in medicaments.

It is known that the NADPH oxidase of phagocytes is the physiological source to the superoxide radical anion and reactive oxygen species derived therefrom which are important in the defence against pathogens. Uncontrolled formation leads to tissue damage in inflammatory processes. It is additionally known that elevation of phagocyte cyclic AMP leads to inhibition of oxygen radical production and that this cell function is more sensitive than others such as aggregation or enzyme release (cf. Inb. Arch. Allergy Immunol., vol. 97: pp 194–199, 1992).

Benzofuran- and benzothiophene derivatives having lipoxygenase-inhibiting action are described in the publication EP 146 243.

Surprisingly it was found that compounds given by the general formula (I) inhibited oxygen radical formation and elevated cellular cyclic AMP levels probably by inhibition of phagocyte phosphodiesterase activity.

The invention relates to Oxalylamino-benzofuran- and benzothienyl-derivatives of the general formula (I)

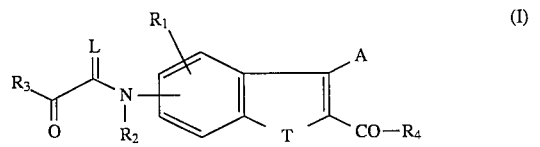

in which

L represents an oxygen or sulfur atom, $R^1$ represents hydrogen or straight-chain or branched alkyl having up to 6 carbon atoms or represents halogen, carboxyl, cyano, nitro, trifluoromethyl or a group of a formula —$OR^5$, —$SR^6$ or —$NR^7R^8$, in which $R^5$, $R^6$ and $R^8$ are identical or different and denote hydrogen, cycloalkyl having 3 to 6 carbon atoms, benzyl or a 5 to 7-membered saturated or unsaturated heterocycle having up to 3 heteroatoms from the series comprising N, S and O and to which a phenyl ring can be fused and which is optionally substituted by identical or different substituents from the series comprising halogen, cyano, nitro or by a straight-chain or branched alkyl having up to 6 carbon atoms, or denote straight-chain or branched alkyl or alkenyl each having up to 8 carbon atoms, or denote phenyl, which is optionally monosubstituted to disubstituted by identical or different substituents from the series comprising nitro, halogen, carboxy or straight-chain or branched alkoxycarbonyl having up to 6 carbon atoms, or $R^5$ denotes a hydroxyl protecting group, and $R^7$ denotes hydrogen or a straight-chain or branched alkyl having up to 4 carbon atoms, $R^2$ represents hydrogen or straight-chain or branched alkyl having up to 6 carbon atoms, $R^3$ represents hydroxyl, benzyloxy or straight-chain or branched alkyl or alkoxy each having up to 10 carbon atoms, and each of which is optionally monosubstituted to trisubstituted by identical or different substituents from the series comprising halogen, carboxyl, trifluoromethyl, phenyl, cyano, or straight-chain or branched alkoxy or oxyacyl each having up to 6 carbon atoms, morpholinyl or by a residue of a formula

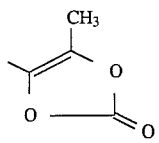

or represents aryl having 6 to 10 carbon atoms, which is optionally monosubstituted to trisubstituted by identical or different substituents from the series comprising halogen, cyano, nitro, carboxyl, straight-chain or branched alkyl, alkoxy, alkoxycarbonyl or acyl each having up to 6 carbon atoms, or represents a group of a formula —$NR^9R^{10}$, in which $R^9$ and $R^{10}$ are identical or different and denote hydrogen, cycloalkyl having 3 to 6 carbon atoms or denote straight-chain or branched alkyl having up to 8 carbon atoms, which is optionally monosubstituted to trisubstituted by identical or different substituents from the series comprising carboxy, straight-chain or branched alkoxy, alkoxycarbonyl or acyl each having up to 6 carbon atoms or phenyl, or denote aryl having 6 to 10 carbon atoms, which is optionally monosubstituted to trisubstituted by identical or different substituents from the series comprising halogen, cyano, nitro, carboxy, straight-chain or branched alkyl, alkoxy, alkoxycarbonyl or acyl each having up to 6 carbon atoms, or denote a group of a formula —$SO_2R^{11}$, in which $R^{11}$ denotes straight-chain or branched alkyl having up to 6 carbon atoms, which is optionally substituted by phenyl, or denotes phenyl, which is optionally substituted by trifluoromethyl, cyano, nitro or straight-chain or branched alkyl having up to 6 carbon atoms, or $R^3$ represents a residue of a formula

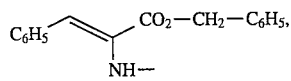

T represents an oxygen or sulfur atom,

A represents hydrogen, hydroxyl, cycloalkyl having up to 6 carbon atoms, carboxy or straight-chain or branched alkoxy or alkoxycarbonyl each having up to 6 carbon atoms, or represents straight-chain or branched alkyl or alkenyl each having up to 8 carbon atoms and each of which is optionally monosubstituted by cyano or by a 5 to 7-membered saturated or unsaturated heterocycle having up to 4 heteroatoms from the series comprising N, S and O, which is optionally substituted by identical or different substituents from the series comprising hydroxy, halogen, cyano, nitro or by a straight-chain or branched alkyl having up to 6 carbon atoms, or alkyl and/or alkenyl are optionally substituted by a group of a formula

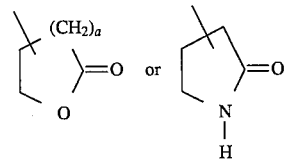

in which a denotes a number 1 or 2 and in which both rings are optionally monosubstituted by hydroxy, halogen or by straight-chain or branched alkyl having up to 6 carbon atoms, or alkyl and/or alkenyl are optionally monosubstituted by a group of a formula $-CO-R^{12}$, $-CO-NR^{13}R^{14}$, $-CONR^{15}-SO_2-R^{16}$ or $-PO(OR^{17})(OR^{18})$,

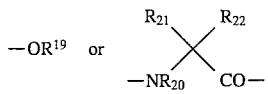

in which $R^{12}$ denotes hydroxyl, cycloalkyloxy having up 3 to 7 carbon atoms or straight-chain or branched alkyl or alkoxy each having up to 8 carbon atoms, $R^{13}$, $R^{14}$ and $R^{15}$ are identical or different and represent hydrogen, a straight-chain or branched alkyl having up to 6 carbon atoms, phenyl or benzyl, or $R^{13}$ denotes hydrogen and $R^{14}$ denotes a 5- to 7-membered saturated or unsaturated heterocycle having up to 3 heteroatoms from the series comprising N, S and O, hydroxyl or a residue of the formula

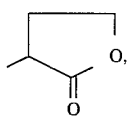

or $R^{13}$ and $R^{14}$ together with the nitrogen atom form a 5- or 6-membered saturated heterocycle, $R^{16}$ denotes a straight-chain or branched alkyl having up to 6 carbon atoms, which is optionally substituted by phenyl or trifluoromethyl, or denotes phenyl, which is optionally substituted by substituents from the series comprising halogen, cyano, nitro or by a straight-chain or branched alkyl having up to 6 carbon atoms, $R^{17}$, $R^{18}$ and $R^{19}$ are identical or different and represent hydrogen or straight-chain or branched alkyl having up to 6 carbon atoms, $R^{20}$ denotes hydrogen, an aminoprotecting group or straight-chain or branched alkyl having up to 6 carbon atoms, $R^{21}$ and $R^{22}$ are identical or different and denote hydrogen or straight-chain or branched alkyl having up to 4 carbon atoms, or $R^{21}$ has the abovementioned meaning and $R^{22}$ denotes cycloalkyl having 3 to 6 carbon atoms or aryl having up 6 to 10 carbon atoms or straight-chain or branched alkyl having up to 8 carbon atoms, which is optionally substituted by cyano, methylthio, hydroxy, mercapto, guanidyl or a group of a formula $-NR^{23}R^{24}$ or $R^{25}-CO-$, wherein $R^{23}$ and $R^{24}$ have the meaning shown above for $R^{13}$, $R^{14}$ and $R^{15}$ and are identical to the latter or different from the latter $R^{25}$ denotes hydroxyl, benzyloxycarbonyl, straight-chain or branched alkoxy having up to 6 carbon atoms or the abovementioned group $-NR^{23}R^{24}$ or alkyl is optionally substituted by cycloalkyl having 3 to 6 carbon atoms, or by aryl having 6 to 10 carbon atoms, which is optionally substituted by hydroxyl, halogen, nitro, straight-chain or branched alkoxy having up to 8 carbon atoms or by the abovementioned group of the formula $-NR^{23}R^{24}$ or alkyl is optionally substituted by indolyl or by a 5 to 6 membered unsaturated heterocycle having up to 3 N-atoms wherein optionally all $-NH-$functions are protected by straight-chain or branched alkyl having up to 6 carbon atoms or by an amino protecting group, or A represents a group of the formula $-CONR^{13'}R^{14'}$, in which $R^{13'}$ and $R^{14'}$ are identical or different and have the abovementioned meaning of $R^{13}$ and $R^{14}$, and $R^4$ represents phenyl, or represents a 5 to 7 membered, saturated or unsaturated heterocycle, which can contain up to 4 oxygen, sulphur and/or nitrogen atoms as heteroatoms and to which further a benzene ring can be fused and wherein all rings are optionally monosubstituted to trisubstituted by identical or different substituents from the series comprising hydroxyl, naphthyl, adamantyl, thiophenyl, cycloalkyl having up to 3 to 6 carbon atoms, halogen, nitro, tetrazolyl, thiazolyl, thienyl, furanyl, pyridyl, trifluoromethyl, phenoxy, difluoromethyl, cyano, carboxy, straight-chain or branched alkyl, alkoxy, alkoxycarbonyl or acyl each having up to 11 carbon atoms or by a group of formula $-NR^{26}R^{27}$, $-SR^{28}$, $SO_2R^{29}$, $-SO_2R^{30}$, $-(CH_2)_b-O-CO-R^{31}$,

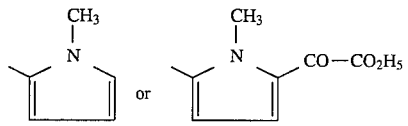

in which $R^{26}$ and $R^{27}$ have the meaning shown above for $R^9$ and $R^{10}$ and are identical to the latter or different from the latter, or $R^{26}$ denotes hydrogen and $R^{27}$ denotes straight-chain or branched acyl having up to 6 carbon atoms $R^{28}$ denotes straight-chain or branched alkyl having up to 6 carbon atoms, $R^{29}$ and $R^{30}$ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, $R^{31}$ denotes straight-chain or branched alkoxycarbonyl or alkyl having up to 6 C-atoms or carboxyl, b denotes a number 0 or 1, or phenyl is optionally substituted by phenyl or phenoxy, which are optionally monosubstituted to trisubstituted by halogen, formyl, nitro, straight-chain or branched alkyl, acyl, hydroxyalkyl, alkoxy or alkoxycarbonyl each having up to 6 C-atoms, or $R^4$ represents adamantyl, cycloalkyl or cycloalkenyl each having up to 6 carbon atoms, and salts thereof.

The Oxalylamino-benzofuran- and benzothienyl-derivatives according to the invention can also be present in the form of their salts. In general, salts with organic or inorganic bases or acids may be mentioned here.

Physiologically acceptable salts are preferred in the context of the present invention. Physiologically acceptable salts of the Oxalylamino-benzofuran- and benzothienyl-derivatives can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid.

Salts of the inventive compounds can also denote, that carboxylic functions can built salts with bases.

Preferably, such bases can be sodium or potassium hydroxide or carbonates, amines or aminacidadducts such as

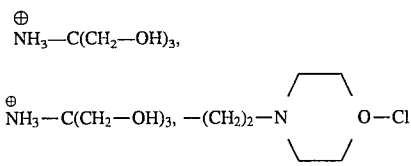

or ammonium

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Hydroxyl protective group in the context of the above-mentioned definition in general represents a protective group from the series comprising: trimethylsilyl, tert.butyl-dimethylsilyl, benzyl, 4-nitrobenzyl, 4-methoxybenzyl, acetyl, tetrahydropyranyl, benzoyl and naphthoyl.

Heterocycle in general represents a 5- to 7-membered saturated or unsaturated, preferably 5- to 6-membered, saturated or unsaturated ring which can contain up to 4 oxygen, sulphur and/or nitrogen atoms as heteroatoms and to which further aromatic ring can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl, dihydrothiazolyl, benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, piperazinyl, oxazolyl, oxazolinyl,triazolyl or tetrazolyl.

Amino protective group in the context of the above mentioned definition in general represents a protective group from the series comprising: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert.butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichlor-tertbutoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloracetyl, 2-bromacetyl, 2,2,2-trifluoracetyl, 2,2,2-trichloracetyl, benzoyl, 4-chlorbenzoyl, 4-brombenzoyl, 4-nitrobenzoyl, phthalimido, isovaleroyl oder benzyloxymethylen, 4-nitrobenzyl, 2,4-dinitrobenzyl or 4-nitrophenyl.

Preferred compounds of the general formula (I) are those in which

L represents an oxygen or sulfur atom, $R^1$ represents hydrogen, straight-chain or branched alkyl having up to 4 carbon atoms or represents fluorine, chlorine, bromine, nitro, trifluoromethyl or a group of a formula —$OR^5$, —$SR^6$ or —$NR^7R^8$, in which $R^7$ denotes hydrogen or a straight-chain or branched alkyl having up to 3 carbon atom, $R^5$, $R^6$ and $R^8$ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by a straight-chain or branched alkyl having up to 5 carbon atoms, denote straight-chain or branched alkyl or alkenyl each having up to 6 carbon atoms, or denote phenyl, which is optionally monosubstituted to disubstituted by identical or different substituents from the series comprising nitro, fluorine, chlorine, bromine, iodine, carboxy or straight-chain or branched alkoxycarbonyl having up to 5 carbon atoms, or $R^5$ denotes benzyl, acetyl or tetrahydropyranyl, $R^2$ represents hydrogen or straight-chain or branched alkyl having up 4 carbon atoms, $R^3$ represents hydroxyl, benzyloxy or straight-chain or branched alkyl or alkoxy each having up to 8 carbon atoms, and each of which is optionally monosubstituted to disubstituted by identical or different substituents from the series comprising fluorine, chlorine, bromine, carboxyl, trifluoromethyl, phenyl, cyano, straight-chain or branched oxyacyl or alkoxy each having up to 4 carbon atoms, morpholinyl or by a residue of a formula

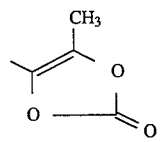

or represents phenyl, which is optionally monosubstituted by substituents from the series comprising fluorine, chlorine, bromine, iodine, cyano, nitro, carboxyl or by a straight-chain or branched alkyl, alkoxy or alkoxycarbonyl each having up to 5 carbon atoms, or represents a group of a formula —$NR^9R^{10}$, in which $R^9$ and $R^{10}$ are identical or different and denote hydrogen, cyclpropyl, cyclopentyl, cyclohexyl, or denote straight-chain or branched alkyl having up to 6 carbon atoms, which is optionally monosubstituted to trisubstituted by identical or different substituents from the series comprising carboxy, straight-chain or branched alkoxy, alkoxycarbonyl or acyl each having up to 5 carbon atoms or phenyl, or denote phenyl, which is optionally monosubstituted to trisubstituted by identical or different substituents from the series comprising fluorine, chlorine, bromine, iodine, carboxy, cyano, nitro or by a straight-chain or branched alkyl, alkoxy or alkoxycarbonyl each having up to 5 carbon atoms, or denote a group of a formula —SO$_2$R$^{11}$ in which R$^{11}$ denotes straight-chain or branched alkyl having up to 4 carbon atoms, which is optionally substituted by phenyl, or denotes phenyl, which is optionally substituted by trifluoromethyl, cyano, nitro or straight-chain or branched alkyl having up to 4 carbon atoms, or R$^3$ represents a residue of a formula

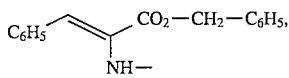

T represents an oxygen or sulfur atom,

A represents hydrogen, cyclopropyl, cyclobutyl, cylcopentyl, hydroxyl, carboxy or straight-chain or a branched alkoxy or alkoxycarbonyl each having up to 5 carbon atoms, or straight-chain or branched alkyl or alkenyl each having up to 6 carbon atoms and each of which is optionally monosubstituted by cyano, tetrazolyl, oxazolyl, oxazolinyl, thiazolyl or a group of a formula

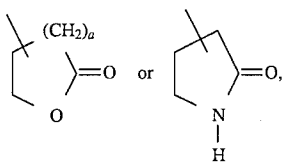

in which a denotes a number 1 or 2, and in which all rings are optionally monosubstituted by hydroxy, fluorine, bromine, chlorine or by straight-chain or branched alkyl having up to 4 carbon atoms, or alkyl or alkenyl are optionally monosubstituted by a group of a formula —CO—R$^{12}$, —CO—NR$^{13}$R$^{14}$, —CONR$^{15}$—SO$_2$—R$^{16}$, —PO(OR$^{17}$)(OR$^{18}$) or —OR$^{19}$ in which R$^{12}$ denotes hydroxyl, cyclopropyloxy, cyclopentyloxy, cyclohexyloxy or straight-chain or branched alkyl or alkoxy each having up to 6 carbon atoms, R$^{13}$, R$^{14}$ and R$^{15}$ are identical or different and represent hydrogen, straight-chain or branched alkyl having up to 4 carbon atoms, phenyl or benzyl, or R$^{13}$ denotes hydrogen, and R$^{14}$ denotes hydroxyl, thiazolyl, dihydrothiazolyl or a residue of the formula

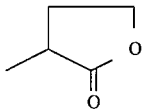

or

R$^{13}$ and R$^{14}$ together with the nitrogen atom form a pyrrolidinyl, morpholinyl or a piperidinyl ring, R$^{16}$ denotes a straight-chain or branched alkyl having up to 5 carbon atoms, which is optionally substituted by phenyl or trifluoromethyl, or denotes phenyl, which is optionally substituted by substituents from the series comprising fluorine, chlorine, bromine, iodine, cyano, nitro or by straight-chain or branched alkyl having up to 4 carbon atoms, R$^{17}$, R$^{18}$ and R$^{19}$ are identical or different and represent hydrogen or straight-chain or branched alkyl having up to 6 carbon atoms, or A represents a group —CONR$^{13'}$R$^{14'}$, in which R$^{13'}$ and R$^{14'}$ have the abovementioned meaning of R$^{13}$ and R$^{14}$ and are identical or different to the latter, and R$^4$ represents phenyl, or represents pyridyl, imidazolyl, pyrazolyl, thienyl, isothiazolyl, 1,3-thiazolyl or benzo[b]thiophenyl, where in all rings are optionally monosubstituted to trisubstituted by identical or different substituents from the series comprising hydroxyl, naphthyl, adamantyl, phenoxy thiophenyl, thienyl, cyclopentyl, cyclohexyl, fluorine, chlorine, bromine, iodine, nitro, tetrazolyl, thiazolyl, furanyl, pyridyl, trifluoromethyl, difluoromethyl, cyano, carboxy, straight-chain or branched alkyl, alkoxy, alkoxycarbonyl or acyl each having up to 10 carbon atoms or by a group of formulae —NR$^{26}$R$^{27}$, —SR$^{28}$, SO$_2$R$^{29}$, —O—SO$_2$R$^{30}$, —(CH$_2$)$_b$ —O—CO—R$^{31}$,

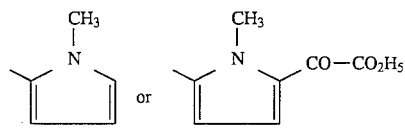

in which

R$^{26}$ and R$^{27}$ have the meaning shown above for R$^9$ and R$^{10}$ and are identical to the latter or different from the latter, or R$^{26}$ denotes hydrogen, and R$^{27}$ denotes straight-chain or branched acyl having up to 6 carbon atoms, R$^{28}$ denotes straight-chain or branched alkyl having up to 4 carbon atoms, R$^{29}$ and R$^{30}$ are identical or different and represent straight-chain or branched alkyl having up to 5 carbon atoms or phenyl, which is optionally substituted by trifluoromethyl, fluorine, chlorine, bromine or straight-chain or branched alkyl having up to 3 carbon atoms, R$^{31}$ denotes straight-chain or branched alkoxycarbonyl or alkyl each having up to 4 carbon atoms or carbonyl, b denotes a number 0 or 1, phenyl is optionally substituted by phenyl or phenoxy, which are optionally monosubstituted to trisubstituted by fluorine, chlorine or bromine, formyl, nitro, straight-chain or branched acyl, alkyl, hydroxyalkyl, alkoxy, alkoxycarbonyl each having up to 4 carbon atoms, or R$^4$ represents adamantyl, cyclopropyl, cyclopentyl, cyclohexyl, cyclopentenyl or cyclohexenyl, and salts thereof.

Particularly preferred compounds of the general formula (I) are those in which

L represents an oxygen or sulfur atom,

R$^1$ represents hydrogen, straight-chain or branched alkyl having up to 3 carbon atoms, fluorine, chlorine, bromine, nitro, trifluoromethyl or a group of a formula —OR$^5$, in which R$^5$ denotes hydrogen, benzyl, acetyl, or denotes straight-chain or branched alkyl each having up to 3 carbon atoms, or denotes phenyl, R$^2$ represents hydrogen or straight-chain or branched alkyl having up to 3 carbon atoms, R³ represents hydroxyl, benzyloxy or straight-chain or branched alkyl or alkoxy each having up to 7 carbon atoms, which is optionally substituted by substituents from the series comprising fluorine, chlorine, bromine, trifluoromethyl, carboxyl, phenyl, cyano, straight-chain or branched alkoxy or oxyacyl each having up to 5 carbon atoms, morpholinyl or by a residue of a formula

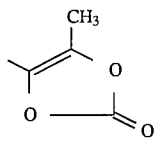

or represents phenyl, which is optionally monosubstituted by different substituents from the series comprising fluorine, chlorine or bromine, or represents a group of a formula —NR⁹R¹⁰, in which
R⁹ and R¹⁰ are identical or different and denote hydrogen, cyclopropyl, cyclopentyl, cyclohexyl or denote straight-chain or branched alkyl having up to 4 carbon atoms, or denote phenyl, or
R³ represents a residue of a formula

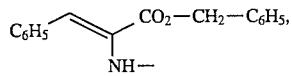

T represents an oxygen atom or sulfur,
A represents hydrogen, cyclopropyl, cyclobutyl, cyclopentyl, hydroxyl, carboxy, or straight-chain or a branched alkoxy or alkoxycarbonyl each having up to 4 carbon atoms, or straight-chain or branched alkyl or alkenyl each having up to 5 carbon atoms and each of which is optionally monosubstituted by cyano, tetrazolyl, oxazolyl, oxazolinyl, thiazolyl or a group of the formula

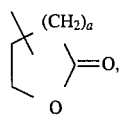

in which
a denotes a number 1 or 2, or alkyl or alkenyl are optionally monosubstituted by a group of a formula —CO—R¹², —CO—NR¹³R¹⁴ or —OR¹⁹, in which
R¹² denotes hydroxyl, cyclopropyloxy, cyclopentyloxy, cyclohexyloxy or straight-chain or branched alkyl or alkoxy each having up to 5 carbon atoms,
R¹³ and R¹⁴ are identical or different and represent hydrogen, straight-chain or branched alkyl having up to 3 carbon atoms, phenyl or benzyl, or
R¹³ denotes hydrogen, and
R¹⁴ denotes hydroxyl, thiazolyl, dihydrothiazolyl or a residue of the formula

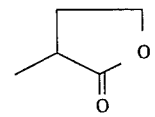

or
R¹³ and R¹⁴ together with the nitrogen atom form a pyrrolidinyl, morpholinyl or piperidinyl ring,
R¹⁹ denotes hydrogen or straight-chain or branched alkyl having up to 4 carbon atoms, or A represents a group of the formula —CONR¹³'R¹⁴', in which
R¹³' and R¹⁴' have the abovementioned meaning of R¹³ and R¹⁴ and are identical or different to the latter, and
R⁴ represents phenyl, or represents pyridyl, thienyl, furyl which are optionally monosubstituted to trisubstituted by identical or different substituents from the series comprising hydroxyl, naphthyl, adamantyl, thiophenyl, cyclopentyl, cyclohexyl, fluorine, chlorine, bromine, nitro, tetrazolyl, thiazolyl, thienyl, furanyl, pyridyl, phenoxy, trifluoromethyl, difluoromethyl, cyano, carboxyl, straight-chain or branched alkyl, alkoxy, alkoxycarbonyl or acyl each having up to 9 carbon atoms or by a group of formulae —NR²⁶R²⁷, SR²⁸ or —(CH₂)$_b$—O—CO—R³¹,

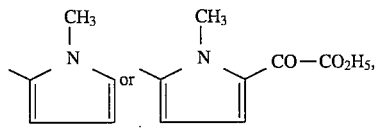

in which
R²⁶ and R²⁷ have the meaning shown above for R⁹ and R¹⁰ and are identical to the latter or different from the latter, or
R²⁶ denotes hydrogen, and
R²⁷ denotes straight-chain or branched acyl having up to 5 carbon atoms,
R28 denotes straight-chain or branched alkyl having up to 4 carbon atoms,
R³¹ denotes straight-chain or branched alkoxycarbonyl or alkyl each having up to 4 carbon atoms or carboxy,
b denotes a number 0 or 1, or
phenyl is optionally substituted by phenyl or phenoxy, which are optionally monosubstituted to trisubstituted by fluorine, chlorine, bromine, nitro, formyl or straight-chain or branched acyl, alkoxy, alkyl, hydroxyalkyl or alkoxycarbonyl, each having up to 3 carbon atoms, or
R⁴ represents adamantyl, cyclopentyl, cyclohexyl, cyclopentenyl or cyclohexenyl.
and salts thereof.

A process for the preparation of the compounds of the general formula (I) has additionally been found, characterized in that at first compounds of the general formula (II)

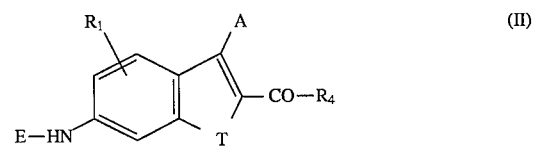

(II)

in which
R¹, R⁴, A and T have the abovementioned meaning and
E represents straight-chain or branched acyl having up to 6 carbon atoms or another typical aminoprotecting group, by elimination of the group E are converted into compounds of the general formula (III)

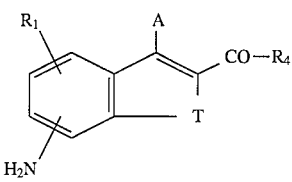

in which

R¹, R⁴, T and A have the abovementioned meaning, which in a further step are reacted with compounds of the general formula (IV)

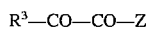

in which

R³ has the abovementioned meaning, and

Z denotes Cl or Br, in inert solvents, if appropriate in the presence of a base and/or in the presence of an auxiliary, and, if appropriate, the protective groups are split off, further amino groups are alkylated, esters are hydrolysed, acids are esterified with the appropriate alcohols in the presence of a catalyst, or the esters directly or the free carboxylic acids are reacted with mines.

The process according to the invention can be illustrated by way of example by the following equations:

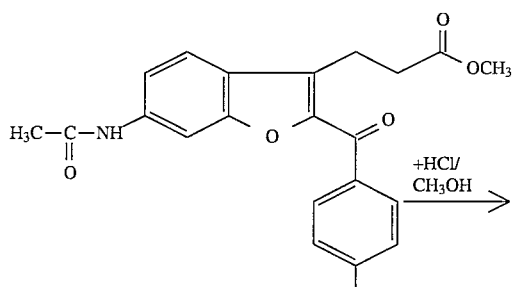

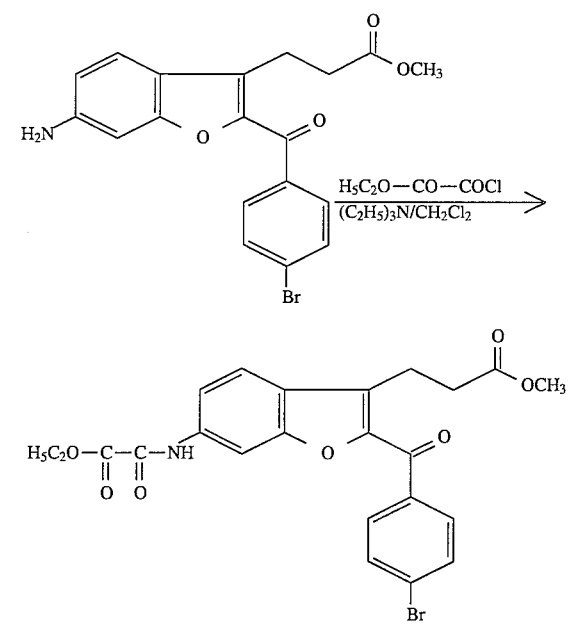

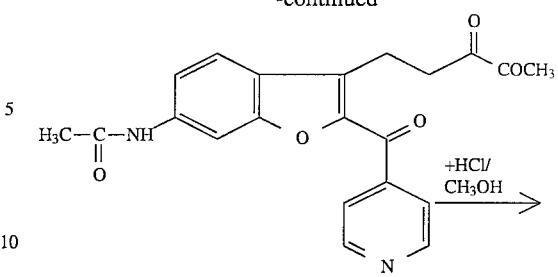

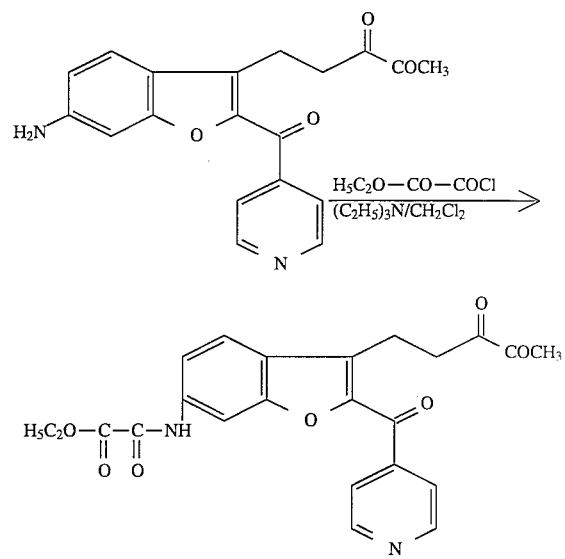

Suitable solvents are generally customary organic solvents which do not change under the reaction conditions. These include ethers such as diethyl ether, dioxane or tetrahydrofurane, acetone, dimethylsulfoxide, dimethylformamide or alcohols such as methanol, ethanol, propanol or halogenohydrocarbons such as dichlormethane, trichloromethane or tetrachloromethane. Methanol and dichloromethane are preferred.

Suitable bases are generally inorganic or organic bases. These preferably include alkali metal hydroxides such as, for example, sodium hydroxide, sodium hydrogencarbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal oder alkaline earth metal alkoxides such as sodium methoxide or potassium methoxide, sodium ethoxide or potassium ethoxide or potassium tert.-butoxide, or organic amines (trialkyl($C_1$–$C_6$)amines) such as triethylamine, or heterocycles such as 1,4-diazabicyclo[2.2.2]octane (DABCO), 1,8-diazabicyclo-[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The process is in general carried out in a temperature range from +10° C. to +150° C., preferably from +20° C. to +60° C.

The process is generally carried out at normal pressure. However, it is also possible to carry out it at elevated pressure or at reduced pressure (for example in a range from 0.5 to 5 bar).

The base is employed in an amount from 1 mol to 10 mol, preferably from 1.0 mol to 4 mol, relative to 1 mol of the compounds of the general formula (III).

The elimination of the amino protective groups is carried out by customary methods, for example by acid in the presence of an alcohol, preferably with HCl/methanole or with p-toluene sulfonic acid/HCl in dimethylformamide.

The elimination of the amino protective groups are in general carried out in a temperature range from −30° C. to +200° C., preferably from +10° C. to 100° C. and at normal pressure.

The compounds of the general formula (II) are new and are prepared by reacting compounds of the general formula (VII)

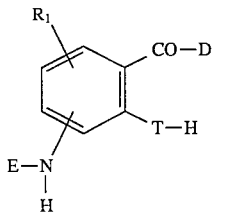
(VII)

in which

R¹, T and E have the abovementioned meaning and

D represents —(CH$_2$)$_2$—(C$_1$–C$_4$)alkoxycarbonyl, with compounds of the general formula (VIII)

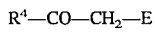
(VIII)

in which

R⁴ has the abovementioned meaning and

E represents a typical leaving group such as, for example, chlorine, bromine, iodine, tosylate or mesylate, preferably bromine, in one of the abovementioned solvents and bases, preferably potassiumcarbonate and dimethylformamide, or in the case of A=CH$_2$—CO—R$^{12}$ first compounds of the general formula (IX)

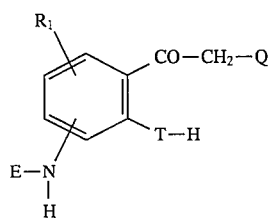
(IX)

in which

E, T and R¹ have the abovementioned meaning, and

Q denotes halogen, preferably chlorine, are converted in the presence of NaAc and and alcohol, preferably ethanol, to compounds of the general formula (X)

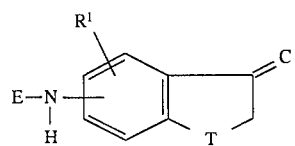
(X)

in which

R¹, E and T have the abovementioned meaning, then are reacted with compounds of the general formula (XI)

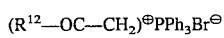
(XI)

in which

R$^{12}$ has the abovementioned meaning to compounds of the general formula (XII)

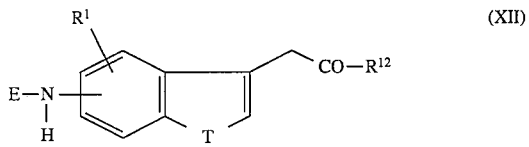
(XII)

in which

E, R¹, T and R$^{14}$ have the abovementioned meaning, in inert solvents, and in a last step are reacted with compounds of the general formula (XIII)

(XIII)

in which

R' denotes a leaving group such as chlorine, bromine, tosylate or mesylate, $^{R4}$ has the abovementioned meaning in the presence of SnCl$_{14}$, and if appropriate in the case of other radicals mentioned under the substituent A, this position is also varied according to the abovementioned methods.

The process is in general carded out in a temperature range from +10° C. to +150° C., preferably from +20° C. to +100° C.

The process is generally carded out at normal pressure. However, it is also possible to carry out it at elevated pressure or at reduced pressure (for example in a range from 0.5 to 5 bar).

The compounds of the general formula (III) are new and are prepared by the abovementioned process.

The compounds of the general formulae (IV), (V), (VI), (VIII), (XI) and (XIII) are known.

The compounds of the general formulae (VII), (IX) and (X) are known in some cases or new and can be prepared by customary methods.

The compounds of the general formula (XII) are new and can be prepared by the abovementioned process.

The compounds according to the invention specifically inhibit the production of superoxide by polymorphonuclear leucocytes (PMN) without impairing other cell functions such as degranulation or aggregation. The inhibition was mediated by the elevation of cellular cAMP probably due to inhibition of the type IV phosphodiesterase responsible for its degradation They can therefore be employed in medicaments for controlling acute and chronic inflammatory processes.

The compounds according to the invention are preferably suitable for the treatment and prevention of acute and chronic inflammations of the airways, such as emphysema, alveolitis, shock lung, asthma, bronchitis, arteriosclerosis, arthrosis, inflammations of the gastro-intestinal tract and myocarditis. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test description

1. Preparation of human PMN

Blood was taken from healthy subjects by venous puncture and neutrophils were purified by dextran sedimentation and resuspended in the buffered medium.

2. Inhibition of FMLP-stimulated production of superoxide radical anions.

Neutrophils (2.5×10$^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 μM, the DMSO concentration was 0.1% v/v in all wells. After addition of cytochalasin b (5 μg×ml$^{-1}$) the plate was incubated for 5 min at 37° C. Neutrophils were then stimulated by addition of 4×10$^{-8}$M FMLP and superoxide generation measured as superoxide dismutase inhibitable reduction of cytochrome C by monitoring the OD$_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - ((Rx - Rb))]}{((Ro - Rb))} \cdot 100$$

Rx=Rate of the well containing the compound according to the invention.

Ro=Rate in the control well.

Rb=Rate in the superoxide dismutase containing blank well.

TABLE A

| Example No. | % Inhibition at 10 μM | IC$_{50}$ [μM] |
| --- | --- | --- |
| 1 | 62 | 0,17 |
| 6 | 67 | 0,11 |
| 7 | 86 | 0,9 |
| 344 | 81 | 0,2 |

3. Measurement of PMN cyclic AMP concentration

The compounds according to the invention were incubated with 3.7×10$^6$ PMN for 5 min at 37° C. before addition of 4×10$^{-8}$M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

4. Assay of PMN phosphodiesterase

PMN suspensions (10$^7$ cells/ml) were sonicated for 6×10 sec on ice. Aliquots (100 μl) were incubated for 5 min at 37° C. with the compounds according to the invention or vehicle before the addition of $^3$H-cAMP (1 mM and 200 nCi per incubation). After 20 min the reaction was stopped by heating at 100° C. for 45 seconds. After cooling 100 mg of 5'-nucleotidase was added to each tube and the samples incubated for 15 min at 37° C. The conversion to $^3$H-adenosine was determined by ion-exchange chromatography on Dowex AG-1x (chloride form) followed by liquid scintillation counting. Percentage inhibition was determined by comparison to vehicle containing controls.

5. Effect of intravenously administered compounds on the FMLP-induced skin oedema guinea pigs Guinea pigs (600–800 g) were anaesthetized with pentobarbitone sodium (40 mg/kg, i.p.) and injected (i.v.) with a 0.5 ml mixture of pentamine sky blue (5% W/V) and $^{125}$I-HSA (1 μli/animal). 10 minutes later 3 intradermal injections of FMLP (10 μg/site), 1 injection of histamine (1 μg/site) and 1 injection of vehicle (100 μl of 0.2% DMSO V/V in Hanks Buffered salt solution) were made on the left hand side of the animal (preinjection sites). 5 minutes later the drug (1 ml/kg) or the vehicle (50% PEG 400 V/V in distilled water, 1 mg/kg) was administered (i.v.). 10 minutes later an identical pattern of interadermal injections was made on the opposite flank of the animal (post-injection sites). These responses were allowed-to develop for 15 minutes before the animal was sacrificed and a blood sample taken.

Skin sites and plasma samples were counted for 1 minute on a gamma counter an the degree of oedema calculated as μl plasma/skin site. Statistical analysis was done by a paired t-test on the mean of the 3 preinjection site values of μl plasma obtained for FMLP/animal. The percentage inhibition of drug or vehicle was calculated as follow

TABLE B

| $X \% = 1 - \dfrac{\overline{X} \text{ μl plasma (post-injection site)}}{\overline{X} \text{ μl plasma (pre-injection site)}} \times 100$ | | |
| --- | --- | --- |
| Example No. | % inhibition | (mg/kg) |
| 2 | 47 | (1) |

6. Effect of orally administered compounds on the FMLP-induced skin oedema of guinea-pigs in vivo Test's p.o.

Guinea-pigs (600–800 g) were fasted overnight and orally treated with vehide (1% Tylose w/v at 5 ml/kg) or drug (10 mg/kg; 2 mg/ml in 1% Tylose at 5 ml/kg) 40 minutes later the animals were anaestized with pentobarbitone sodium (40 mg/kg, i.P.) and 0.6 ml of a mixture of pontamine sky blue (5% w/v) and $^{125}$I-HSA (1 μci/animal) was injected (i.v.). 90 minutes after oral pretreatment FMLP (50 μg/site) was injected (i.d.) at 4 different sites, histamine (1 μg/site) and vehicle (100 μl, 1% DMSO v/v in Hanks buffered salt solution) were both injected (i.d.) at 2 different sites.

The responses were allowed to develop for 30 minutes before the animal was sacrificed and a blood sample taken. Skin sites and plasma samples were counted for 1 minute on a gamma counter. The degree of oedema was calculated as μl plasma/skin site. Statistical analysis was carried out by a Mann-Whitney U-test on the mean of the 4 values of μl Plasma obtained for FMLP/animal.

TABLE C

| Example No. | % inhibition | (mg/kg) |
| --- | --- | --- |
| $\dfrac{[1 - ((Rx - Rb))]}{((Ro - Rb))} \cdot 100$ | 48 | (10) |
| 7 | | |

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day.

| Solvents | |
|---|---|
| I | petrolether:ethylacetate 1:1 |
| II | petrolether:ethylacetate 5:1 |
| III | petrolether:ethylacetate 5:2 |
| IV | dichlormethane:methanol 95:5 |
| V | dichlormethane:methanol 5:1 |
| DMF | dimethylformamide |

Starting compounds

EXAMPLE I

4-Acetamido-2-hydroxy-γ-oxo-benzen-butanoic acid, methylester

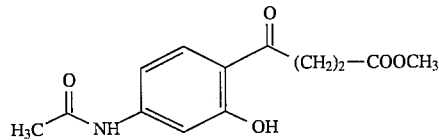

67.5 g (0.41 mol) 3-acetamidoanisol are suspended in 200 ml 1,2-dichloroethane and cooled in an ice bath. 217 g (1.64 mol) $AlCl_3$ and after it 73.9 g (0.49 mol) 3-carbomethoxypropionylchloride were added successively. Stirring was continued ½ hour. After 5 hours the reaction was quenched with ice and ethylacetate and water were added. The organic layer was seperated, washed with water, dried over $MgSO_4$ and concentrated in vacuo. The residue was recrystallized from dioxane and water.

Yield: 52 g (49% of theory)

EXAMPLE II

3-[6-Acetamido-2-(4-chloro-benzoyl)-3-benzofuranyl]propanoic acid, methylester

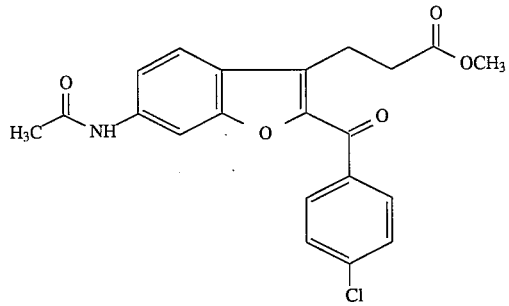

1.5 g (3.75 mmol) of 2'-Hydroxy-3-oxo-4'-[(acetamido)]benzenebutanoic acid, methylester and 1,13 g (4.1 mmol) of 2-bromo-4'-chloroacetophenone were dissolved in 5 ml DMF and 1,55 g (11.25 mmol) of potassium carbonate were added. The suspension was heated to 60° C. for 1 h, ethylacetate was added. The organic phase was washed three times with water, one time with a NaCl solution, dried over $Na_2SO_4$ and concentrated in vacuo. The residue was further purified by crystallisation (ethanol).

Yield: 0.75 g (50%)

$R_f$=0,12, (III)

EXAMPLE III

3-[6-Amino-2-(4-chloro-benzoyl)-3-benzofuranyl]propanoic acid, methylester

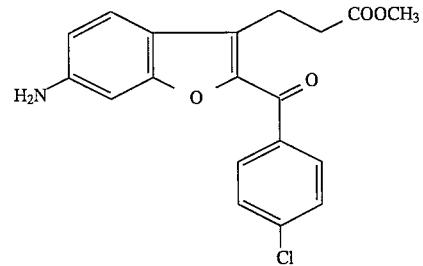

3.1 g (7.7 mmol) of 2-(4-chloro-benzoyl)-6-acetamido-3-benzofuranpropanoic acid methylester were suspended in 40 ml methanol. 20 ml 2.6N HCl was added with stirring. The reaction mixture was heated to reflux. After 1 hour a clear solution was obtained. After 3 hours reflux the solution was cooled to room temperature and ethylacetate added. The organic layer was washed with NaOH-solution, two times with water, dried with $Na_4SO_4$ and concentrated in vacuo. The residue was further purified by crystallisation.

Yield: 2,26 g (82%)

$R_f$: 0.34 (III)

TABLE I

The compounds shown in Table I are prepared in analogy to the procedure of Example III.

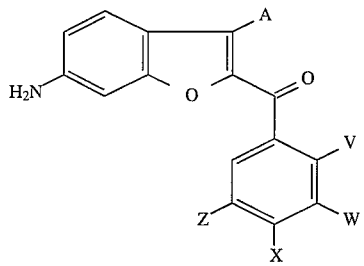

| Ex. No. | V | W | X | Z | A | $R_f$* | Yield (% of theory) |
|---|---|---|---|---|---|---|---|
| IV | H | H | Cl | H | $(CH_2)_2COOH$ | 0.78 (V) | 98 |
| V | H | H | F | H | $(CH_2)_2COOCH_3$ | 0.69 (V) | 88 |
| VI | H | CN | H | H | $(CH_2)_2CO_2CH_3$ | 0.66 (V) | 76 |
| VII | H | $CH_3$ | Cl | H | $(CH_2)_2COOCH_3$ | 0.8 (V) | 76 |
| VIII | H | H | CN | H | $(CH_2)_2COOCH_3$ | 0.7 (V) | 67 |
| IX | H | Cl | H | H | $(CH_2)_2COOCH_3$ | 0.79 (V) | 75 |
| X | H | $OCH_3$ | H | H | $(CH_2)_2COOCH_3$ | 0.65 (V) | 58 |
| XI | H | H | $SCH_3$ | H | $(CH_2)_2COOCH_3$ | 0.81 (V) | 84 |
| XII | H | H | $NO_2$ | H | $(CH_2)_2COOCH_3$ | 0.70 (V) | 75 |
| XIII | Cl | H | Cl | H | $(CH_2)_2COOCH_3$ | 0.85 (V) | 75 |
| XIV | H | Br | H | H | $(CH_2)_2COOCH_3$ | 0.71 | 77 |
| XV | H | H | Br | H | $(CH_2)_2COOCH_3$ | 0.70 | 76 |
| XVI | H | H | Cl | H | ⁀⁀CN | 0.74 (IV) | 90 |
| XVII |   | H | Cl | H | ⁀⁀$CONH_2$ | 0.5 (IV) | 80 |
| XVIII | H | H | $C_4H_9$ | H | $-CH_2CO_2C_2H_5$ | 0.42 (I) | 72 |
| XIX | H | H | $CH_3$ | H | $-CH_2-CO_2C_2H$ | 0.46 (I) | 80 |
| XX | H | H | $C_6H_5$ | H | $-CH_2-CO_2C_2H_5$ | 0.54 (I) | 77 |
| XXI | Cl | H | Cl | H | $-CH_2-CO_2C_2H_5$ | 0.46 (I) | 81 |

TABLE II

The compounds shown in Tables II and III are prepared in analogy to the procedure of example III

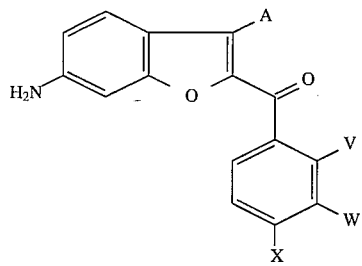

| Ex. No. | A | V | W | X | Rf* | Yield (% of theory) |
|---|---|---|---|---|---|---|
| XXII | cyclopropyl | H | $CH_3$ | H | 0,77 (I) | 87 |
| XXIII | $-OH$ | H | Br | H | 0,43 (VI) | 70 |
| XXIV | cyclobutyl | H | $-OCH_3$ | H | 0,7 (I) | 97 |
| XXV | $-H$ | H | H | $CH_3$ | 0,7 (I) | 84 |
| XXVI | $-C_2H_5$ | H | $OCH_3$ | H | 0,69 (I) | 89 |
| XXVII | cyclopropyl | H | $OCH_3$ | H | 0,71 (I) | 87 |
| XXVIII | $-OC_2H_5$ | H | H | $CH_3$ | 0,69 (I) | 89 |

TABLE II-continued

The compounds shown in Tables II and III are prepared in analogy to the procedure of example III

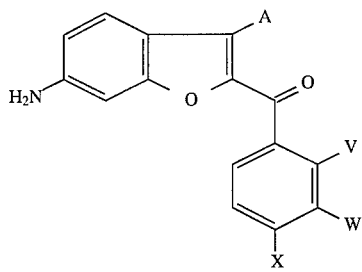

| Ex. No. | A | V | W | X | Rf* | Yield (% of theory) |
|---|---|---|---|---|---|---|
| XXIX | cyclobutyl | H | CF₃ | H | 0,82 (I) | 64 |
| XXX | cyclobutyl | Cl | H | Cl | 0.80 (I) | 89 |
| XXXI | cyclopropyl | H | CF₃ | H | 0,44 (VI) | 62 |
| XXXII | cyclopropyl | H | Br | H | 0.90 (I) | 70 |
| XXXIII | cyclopropyl | Cl | H | Cl | 0.90 (I) | 94 |
| XXXIV | —C₂H₅ | H | CH₃ | H | 0.71 (I) | 75 |
| XXXV | cyclobutyl | H | CH₃ | H | 0.65 (I) | 82 |
| XXXVI | CH₂CO₂Et | Cl | H | Cl | 0,468 (I) | 80 |
| XXXVII | CH₂CO₂Et | H | H | Cl | 0,4 (I) | 89,6 |
| XXXVIII | CH(CH₃)₂ | H | H | OCH₃ | 0,365 (I) | 82,3 |
| XXXIX | CH(CH₃)₂ | OCH₃ | H | OCH₃ | 0,308 (I) | 76 |
| XL | CH₂COOEt | H | H | CH₃ | 0,452 | 72,6 |
| XLI | cyclopropyl | OCH₃ | H | OCH₃ | 0,31 (IV) | 86,1 |
| XLII | cyclopropyl | H | H | OCH₃ | 0,45 (IV) | 58,4 |
| XLIII | cyclopropyl | H | H | Br | 0,614 (IV) | 85,7 |
| XLIV | cyclopropyl | H | H | phenyl | 0,61 (IV) | 88,3% |
| XLV | cyclopropyl | H | H | CH₃ | 0,74 (I) | 73 |
| XLVI | cyclopropyl | H | CN | H | 0,85 (I) | 91 |
| XLVII | cyclobutyl | H | H | F | 0,74 (I) | 70 |

TABLE II-continued

The compounds shown in Tables II and III are prepared in analogy to the procedure of example III

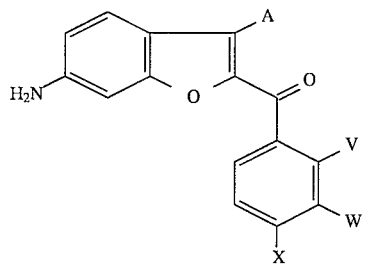

| Ex. No. | A | V | W | X | Rf* | Yield (% of theory) |
|---|---|---|---|---|---|---|
| XLVIII | cyclobutyl | H | H | cyclohexyl | 0,6 (IV) | 97 |
| XLIX | cyclopropyl | H | H | cyclohexyl | 0,55 (III) | 97 |
| L | cyclopropyl | H | H | F | 0,54 (I) | 85 |
| LI | —CH(CH₃)₂ | H | H | NO₂ | 0,9 (I) | 96 |
| LII | —CH(CH₃)₂ | H | H | CH₃ | 0,71 (I) | 73 |
| LIII | —CH(CH₃)₂ | H | H | OCH₃ | 0,65 (I) | 97 |
| LIV | —CH(CH₃)₂ | Cl | Cl | H | 0,58 (III) | 41 |
| LV | —CH(CH₃)₂ | CH₃ | CH₃ | H | 0,54 (III) | 72 |
| LVI | —CH(CH₃)₂ | H | H | CF₃ | 0,60 (III) | 61 |
| LVII | —C₂H₅ | H | Br | H | 0,5 (III) | 89 |
| LVIII | —C₂H₅ | H | H | CN | 0,74 (I) | 54 |
| LIX | —C₂H₅ | H | CN | H | 0,88 (I) | 45 |
| LX | —C₂H₅ | H | H | C₂H₅ | 0,42 (III) | 100 |
| LXI | —C₂H₅ | H | H | cyclohexyl | 0,73 (I) | 72,5 |
| LXII | —C₂H₅ | H | H | F | 0,76 (I) | 100 |
| LXII | —CH(CH₃)₂ | H | H | Br | 0,35 (III) | 98 |
| LXIV | —CH(CH₃)₂ | H | Br | H | 0,44 (III) | 95 |
| LXV | —CH(CH₃) | H | H | C₂H₅ | 0,52 (III) | 93 |
| LXVI | —CH(CH₃)₂ | H | H | cyclohexyl | 0,56 (III) | 91 |
| LXVII | —CH(CH₃)₂ | H | H | F | 0,8 (I) | 95 |
| LXVIII | —CH(CH₃)₂ | H | H | C₆H₅ | 0,79 (IV) | 95 |

TABLE III

| Ex. No. | X | Rf* | Yield (% of theory) |
|---|---|---|---|
| LXIX | C₂H₅ | 0,82 (IV) | 80 |
| LXX | CH₃ | 0,57 (I) | 62 |
| LXXI | 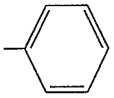 | 0,65 (I) | 92 |
| LXXII | F | | |
| LXXIII | OCH₃ | | |
| LXXIV | 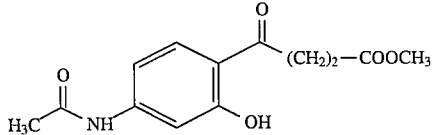 | | |

EXAMPLE LXXV

4-Acetamido-2-hydroxy-γ-oxo-benzen-butanoic acid, methylester

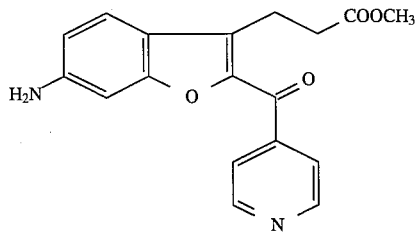

67.5 g (0.41 mol) 3-acetamidoanisol are suspended in 200 ml 1,2-dichloroethane and cooled in an ice bath. 217 g (1.64 mol) AlCl₃ and after it 73.9 g (0.49 mol) 3-carbomethoxypropionylchloride were added successively. Stirring was continued ½ hour. After 5 hours the reaction was quenched with ice and ethylacetate and water were added. The organic layer was seperated, washed with water, dried over MgSO₄ and concentrated in vacuo. The residue was recrystallized from dioxane and water.

Yield: 52 g (49% of theory)

EXAMPLE LXXVI

3-[6-Acetamido-2-(pyridine-4-carbonyl)benzofuran-3-yl]propionic acid, methylester

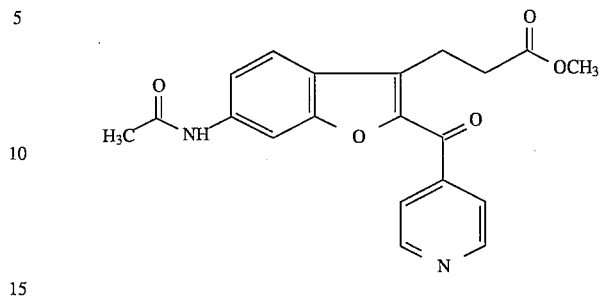

1.5 g (3.75 mmol) of 2'-hydroxy-3-oxo-4'-[(acetamido)]benzenebutanoic acid, methylester and 0.82 g (4.1 mmol) of 2-bromo-1-(4-pyridyl)-ethanone were dissolved in 5 ml DMF and 1,55 g (11.25 mmol) of potassium carbonate were added. The suspension was heated to 50° C. for 1 h, ethylacetate was added. The organic phase was washed three times with water, one time with a NaCl solution, dried over Na₂SO₄ and concentrated in vacuo. The residue was further purified by chromatography.

Yield: 0.412 g (30%)

$R_f$=0,1, (I)

EXAMPLE LXXVII

3-[6-Amino-2-(pyridine-4-carbonyl)-3-benzofuranyl]propanoic acid, methylester 2.8 g (7.7 mmol) of 2-(4-chloro-benzoyl)-6-acetamido-3-benzofuranpropanoic acid methylester were suspended in 40 ml methanol. 20 ml 2.6N HCl was added with stirring. The reaction mixture was heated to reflux. After 1 hour a clear solution was obtained. After 3 hours reflux the solution was cooled to room temperature and ethylacetate added. The organic layer was washed with NaOH-solution, two times with water, dried with Na₂SO₄ and concentrated in vacuo. The residue was further purified by crystallisation.

Yield: 1.64 g (60%)

$R_f$: 0.34 (III)

TABLE IV

The compounds shown in Table IV are prepared in analogy to the procedure of example II:

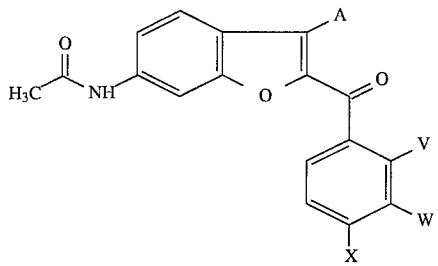

| Ex.-No. | V | W | X | A | $R_f$* | Yield (% of theory) |
|---------|---|---|---|---|--------|---------------------|
| LXXVIII | Cl | H | Cl | COOC$_2$H$_5$ | 0,53 (IV) | 72 |
| LXXIX | H | H | F | CH$_2$CH$_2$COOCH$_3$ | 0,29 (I) | 28 |
| LXXX | H | H | CN | CH$_2$CH$_2$COOCH$_3$ | 0,22 (I) | 46 |
| LXXXI | H | CH$_3$ | Cl | CH$_2$CH$_2$COOCH$_3$ | 0,23 (I) | 66 |
| LXXXII | H | H | SCH$_3$ | CH$_2$CH$_2$COOCH$_3$ | 0,31 (I) | 52 |
| LXXXIII | H | Cl | H | CH$_2$CH$_2$COOCH$_3$ | 0,24 (I) | 58 |
| LXXXIV | H | OCH$_3$ | H | CH$_2$CH$_2$COOCH$_3$ | 0,18 (I) | 68 |
| LXXXV | H | H | Cl | CO$_2$C$_2$H$_5$ | | |

EXAMPLE LXXXVI

N-[2-(4-Chloro-benzoyl)-3-(2-methoxycarbonyl-ethyl)-benzofuran-6-yl]-malonamic acid methyl ester

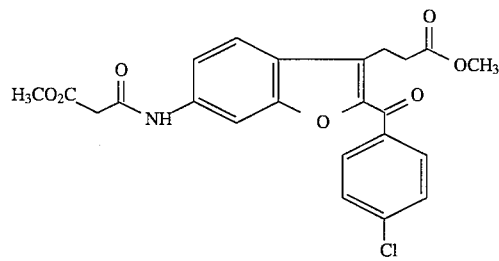

a)
3-[6-Amino-2-(4-chloro-benzoyl)-3-benzofuranyl]propanoic acid, methylester 3.1 g (7.7 mmol) of 2-(4-chloro-benzoyl)-6-acetamido-3-benzofuranylpropanoic acid methylester were suspended in 40 ml methanol. 20 ml 2.6N HCl were added with stirring. The reaction mixture was heated to reflux. After 1 hour a clear solution was obtained. After 3 hours reflux the solution was cooled to room temperature and ethylacetate was added. The organic layer was washed with NaOH-solution, two times with water, dried over Na$_2$SO$_4$ and concentrated in vacuo. The residue was further purified by crystallisation.

Yield: 2.26 g (82%)

$R_f$: 0.34 (III)

b)

0.5 g (1.4 mmol) of 3-[6-Amino-2-(4-chloro-benzoyl)-3-benzofuranyl]propanoic acid methylester were dissolved in 20 ml methylenechloride and 4 ml triethylamine(EtN$_3$). 0.6 g (4.5 mmol) (Cl—CO—CH$_2$—COOCH$_3$) methylmalonylchloride were added dropwise. The mixture was heated to reflux for 12 h. After removing the solvent, ethylacetate and water were added. The organic layer was washed twice with water and NaCl-solution, dried over Na$_2$SO$_4$ and concentrated in vacuo. The residue was further purified by recrystallisation (methanol).

Yield: 0.4 g (62.5%)

$R_f$: =0.88 (V)

The compounds shown in table V were prepared in analogy to the procedure of example LXXVIII:

TABLE V

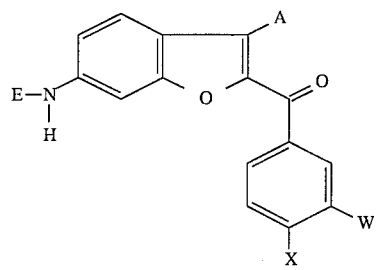

| Ex.-No. | W | X | A | E | R$^3$ | $R_f$* | Yield (% of theory) |
|---------|---|---|---|---|-------|--------|---------------------|
| LXXXVII | H | Cl | CH$_2$CH$_2$COOCH$_3$ | COCH$_2$CH$_2$COOCH$_3$ | H | 0.3 (III) | 61 |

EXAMPLE LXXXVII

3-[6-Acetamido-2-(4-chlorobenzoyl)-3-benzo-furanyl]propanoic acid

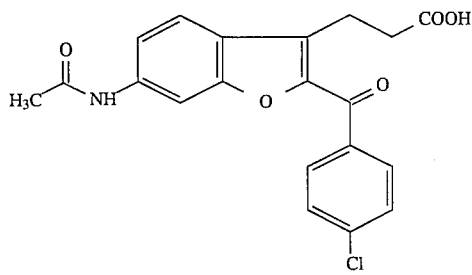

1.5 g (4.2 mmol) of the compound from starting compounds Example III were dissolved in 50 ml methanol/tetrahydrofuran (1:1) and 5.5 ml of a 2N NaOH solution were added. The mixture was stirred at r.t. for 24 hours, dissolved in water and acidified with 1N hydrochloric acid. The precipitate was filtered off, washed several times with water and dried in vacuo. The further reaction was carried out as described in Example 1.

Yield: 96%

$R_f$: 0,54 (V)

The compounds shown in Table VI were prepared in analogy to the procedure of Example LXXXVIII:

TABLE VI

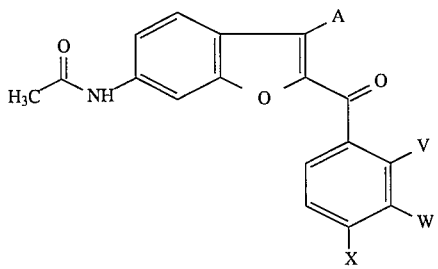

| Ex.-No. | V | W | X | A | $R_f$* | Yield (% of theory) |
|---|---|---|---|---|---|---|
| LXXXIX | H | H | Cl | CH$_2$CH$_2$CO$_2$Na | 0,58 (IV) | 98 |
| XC | H | H | SCH$_3$ | CH$_2$CH$_2$COOH | 0,68 (V) | 88 |
| XCI | H | H | F | CH$_2$CH$_2$COOH | 0,51 (V) | 83 |
| XCII | H | Cl | H | CH$_2$CH$_2$COOH | 0,51 (V) | 95 |
| XCIII | H | OCH$_3$ | H | CH$_2$CH$_2$COOH | 0,54 (V) | 87 |

0.56 g (1.3 mmol) of the acid from example 1 were dissolved in 5 ml THF, 0.25 g (1.25 mmol) 1,1'-carbonyl-bis-1H-imidazole were added and the mixture was stirred at room temperature for 12 hours. Subsequently NH$_3$-gas was added for 2 h using an inlet pipe. After one additional hour stirring at r.t. the solvent was distilled off in vacuo. The residue was taken up in ethylacetate and washed three times with water, one time with a NaHCO$_3$ solution and one time with a NaCl solution. The organic phase was dried over MgSO$_4$ and the solvent was removed in vacuo.

Yield: 83%

$R_f$: 0,72 (V)

EXAMPLE XCIV

3-[6-Acetamido-3-(2-carbonamid-ethyl)-2-(4-chloro-benzoyl)-benzofuran

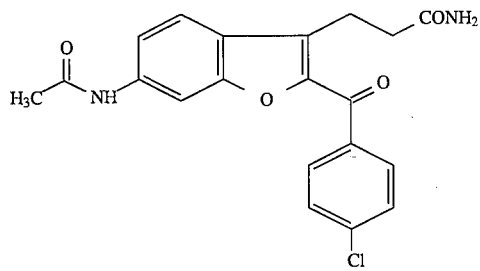

EXAMPLE XCV

3-[6-Acetamido-2-(4-chloro-benzoyl)-3-(2-cyano-ethyl)-benzofuran

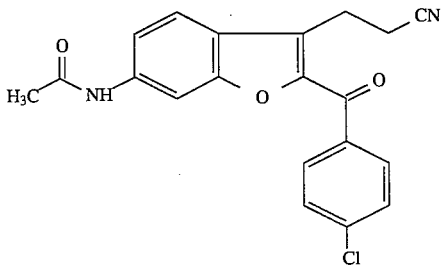

0.56 g (1.3 mmol) of example XCIV were dissolved in 15 ml dioxane. 0.2 ml (2.6 mmol) pyridine were added, cooled to 5°–10° C. and 0.22 ml (1.56 mmol) trifluoroacetic anhydride were added dropwise. The mixture was stirred for 3 hours at room temperature. The mixture was added to water, washed twice with dichloromethane. The organic layer was dried and the solvent removed in vacuo.

Yield: 73%

$R_f$: 0,49 (IV)

The compounds shown in Table VII are prepared by Friedel-Crafts reaction of Example I with (carbethoxymethylene)-triphenylphosphorane in xylene.

TABLE VII

| Example No. | V | W | X | $R_f$* | yield (% of theory) |
|---|---|---|---|---|---|
| XCVI | H | H | —$C_4H_9$ | 0.22 (I) | 31 |
| XCVII | H | H | —$CH_3$ | 0.21 (I) | 86 |
| XCVIII | H | H | —$C_6H_5$ | 0.5 (IV) | 70 |
| XCIX | Cl | H | —Cl | 0.6 (IV) | 97 |
| C | H | H | —Br | 0.25 (I) | 76 |
| CI | HBr | | H | 0.33 (II) | 68 |
| CII | H | CN | H | 0.25 (I) | 75 |

EXAMPLE CIII

N-[3-Methyl-2-(4-methyl-benzoyl)-benzofuran-6-yl]acetamide

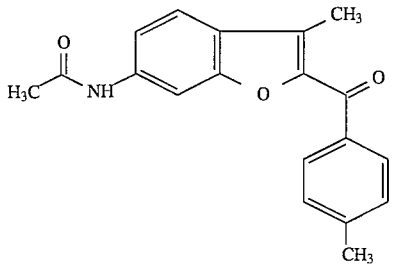

0.72 g (3.75 mmol) of N-(4-acetyl-3-hydroxy-phenyl)-acetamide and 0.81 g (4.1 mmol) of 2-bromo-4-methylacetophenone were dissolved in 5 ml DMF and 1,55 g (11.25 mmol) of potassium carbonate were added. The suspension was heated to 60° C. for 1 h and ethylacetate was added. The organic phase was washed three times with water, one time with a NaCl solution, dried over $Na_2SO_4$ and concentrated in vacuo. The residue was further purified by crystallisation (ethanol).

Yield: 0.58 g (50%)

$R_f$=0,12 (III)

The compounds shown in Table VIII were prepared in analogy to the procedure of Example CIII:

TABLE VIII

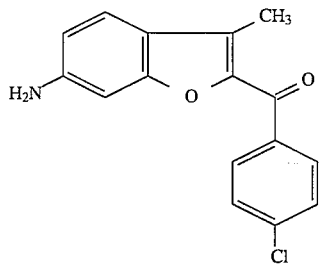

| Ex.-No. | Z | $R^2$ | $R_f$* | Yield (% of theory) |
|---|---|---|---|---|
| CIV | Cl | $COCH_3$ | 0.33 (IV) | 38 |
| CV | $C_6H_5$ | $COCH_3$ | 0.35 (I) | 53 |

EXAMPLE CVI (6-Amino-3-methyl-benzofuran-2-yl)-(4-chlorophenyl)-methanone 3.1 g (10 mmol) of N-[3-methyl-2-(4-methyl-benzoyl)benzofuran-6-yl]-acetamide were suspended in 40 ml methanol. 20 ml 2.6N HCl were added with stirring. The reaction mixture was heated to reflux. After 1 hour a clear solution was obtained. After 3 hours reflux the solution was cooled to room temperature and ethylacetate was added. The organic layer was washed once with NaOH-solution, two times with water, dried over $Na_4SO_4$ and concentrated in vacuo. The residue was further purified by crystallisation.

Yield: 2,2 g (83%

$R_f$: 0.7 (V)

The compounds shown in table IX and X were prepared in analogy to the procedure of example CVI:

TABLE IX

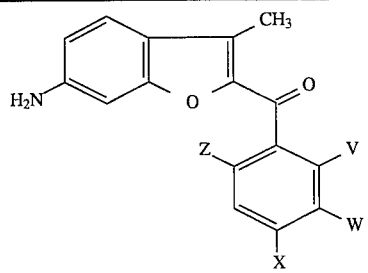

| Ex.-No. | Z | $R_f$* | Yield (% of theroy) |
|---|---|---|---|
| CVII | CH$_3$ | 0.62 (IV) | 87 |
| CVIII | C$_6$H$_5$ | 0.38 | 71 |

TABLE X

| Example No. | X | V | Z | W | $R_f$ | yield |
|---|---|---|---|---|---|---|
| CIX | Cl | H | H | H | 0.3 (I) | 65 |
| CX | CH$_3$ | CH$_3$ | CH$_3$ | H | 0.98 (IV) | 70 |
| CXI | Br | H | H | H | 0.45 (I) | 55 |
| CXII | NO$_2$ | H | H | H | 0.83 (I) | 22 |
| CXIII | H | H | H | CN | 0.38 (IV) | 92 |
| CXIV | CN | H | H | H | 0.77 (I) | 70 |
| CXV | Cl | Cl | H | H | 0.26 (I) | 65 |
| CXVI | H | H | H | NO$_2$ | 0.79 (I) | 88 |
| CXVII | H | H | H | Br | 0.27 (I) | 65 |
| CXVIII | H | H | H | OCH$_3$ | 0.21 (I) | 71 |
| CXIX | H | H | H | CH$_3$ | 0.25 (I) | 73 |
| CXX | H | H | H | CF$_3$ | 0.35 (I) | 37 |
| CXXI | —⟨C$_6$H$_4$⟩—OCH$_3$ | H | H | NO$_2$ | 0.37 (II) | 40 |

The compounds shown in Table XI were prepared in analogy to the procedure of example CIII.

TABLE XI

[Structure: benzofuran with R₂-NH- group, connected via C=O to phenyl ring with Y, W, Z substituents and A group]

| Example No. | Y | Z | W | E | A | R_f | yield |
|---|---|---|---|---|---|---|---|
| CXXII | H | C₆H₅ | H | CONH₂ | CH₃ | 0.18 (I) | 76 |
| CXXIII | H | NO₂ | H | COCH₃ | CH₃ | 0.28 (I) | 63 |
| CXXIV | H | Br | H | COCH₃ | CH₃ | 0.32 (I) | 73 |
| CXXV | H | H | CN | COCH₃ | CH₃ | 0.47 (IV) | 29 |
| CXXVI | H | CN | H | COCH₃ | CH₃ | 0.27 (I) | 13 |
| CXXVII | Cl | Cl | H | COCH₃ | CH₃ | 0.4 (I) | 46 |
| CXXVIII | H | H | NO₂ | COCH₃ | CH₃ | 0.29 (I) | 16 |
| CXXIX | H | H | Br | COCH₃ | CH₃ | 0.37 (I) | 43 |
| CXXX | H | H | OCH₃ | COCH₃ | CH₃ | 0.29 (I) | 76 |
| CXXXI | H | H | CH₃ | COCH₃ | CH₃ | 0.13 (III) | 58 |
| CXXXII | H | H | CF₃ | COCH₃ | CH₃ | 0.13 (III) | 35 |
| CXXXIII | H | —C₆H₄—OCH₃ | | NO₂ | COCH₃ | CH₃ | 0.24 (I) | 7 |

The compounds shown in Table XII are prepared in analogy to the procedure of example LXXVI.

TABLE XII

[Structure: H₃C-C(O)-NH- on benzofuran with A substituent and -C(O)-R₄ group]

| Ex.-No. | A | R⁴ | R_f* | Yield (% of theory) |
|---|---|---|---|---|
| CXXXIV | —COOC₂H₅ | 4-pyridyl | 0,1 (I) | 30 |
| CXXXV | —CH₂CH₂CO₂CH₃ | 3,4,6-trimethyl-2-pyridyl | 0,32 (IV) | 72 |

The compounds shown in Table XIII are prepared in analogy to the procedure of example LXXVII.

TABLE XIII

Structure: benzofuran with H$_2$N- substituent, (CH$_2$)$_2$-CO$_2$CH$_3$ group, and C(=O)R$_4$ group

| Ex.-No. | R$^4$ | R$_f$* | Yield (% of theory) |
|---|---|---|---|
| CXXXVI | 2,4,6-trimethylpyridin-3-yl (H$_3$C, CH$_3$, H$_3$C on pyridine N) | 0.6 (V) | 90 |
| CXXXVII | pyridinyl | 0.32 (IV) | 50 |
| CXXXVIII | pyridinyl | 0.4 (IV) | 75 |
| CXXXIX | 2,4,6-trimethylpyridinyl (CH$_3$, CH$_3$, CH$_3$) | 0.3 (IV) | 95 |

The compounds shown in Table XIV are prepared in analogy to the procedure of example CXL.

TABLE XIV

Structure: benzofuran with H$_3$C-OC-HN- substituent, A group, and C(=O)-OR$^4$ group

| Example No. | A | R$^4$ | R$_f$* | yield |
|---|---|---|---|---|
| CXL | C$_2$H$_4$COOCH$_3$ | pyridinyl | 0.25 (IV) | 30 |
| CXLI | C$_2$H$_4$COOCH$_3$ | pyridinyl | 0.3 (IV) | 20 |
| CXLII | CH$_3$ | 2,4,6-trimethylpyridinyl (CH$_3$, CH$_3$, CH$_3$) | 0.34 (IV) | 63 |

The compounds shown in the Tables XV and XVI are prepared in analogy to the procedure of CVI.

TABLE XV

Structure: benzofuran with NH$_2$, CH$_3$, and C(=O)-phenyl(V,W,X) substituents

| Example No. | V | W | X | R$_f$* | yield (% of theory) |
|---|---|---|---|---|---|
| CXLIII | H | H | F | 0.5 (I) | 98 |
| CXLIV | H | H | Br | 0.5 (III) | 97 |
| CXLV | H | H | C$_2$H$_5$ | 0.44 (I) | 82 |
| CXLVI | H | H | cyclohexyl | 0.5 (I) | 82 |
| CXLVII | Cl | H | Cl | 0.63 (I) | 80 |
| CXLVIII | H | NO$_2$ | H | 0.5 (I) | 70 |
| CXLIX | H | CH$_3$ | H | 0.63 (I) | 94 |
| CL | CH$_3$ | H | CH$_3$ | 0.91 (I) | 81 |
| CLI | H | H | NO$_2$ | 0.83 (I) | 77 |
| CLII | H | CF$_3$ | H | 0.69 (I) | 91 |
| CLIII | H | OCH$_3$ | H | 0.66 (I) | 90 |

TABLE XV-continued
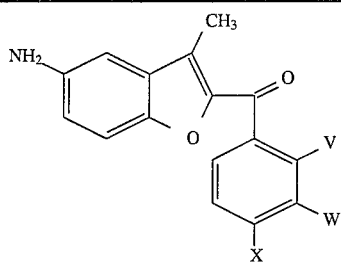
| Example No. | V | W | X | $R_f$* | yield (% of theory) |
|---|---|---|---|---|---|
| CLIV | H |  —OCH₃ | H | 0.42 (I) | 94 |
TABLE XVI
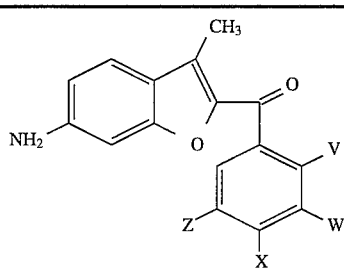
| Ex. No. | V | W | X | Z | $R_f$* | yield (% of theory) |
|---|---|---|---|---|---|---|
| CLV | H | 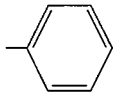 | H | H | 0.63 (I) | 100 |
| CLVI | H | H | C₉H₁₉ | H | 0.84 (V) | 78 |
| CLVII | H | H | C₆H₁₃ | H | 0.80 (V) | 76 |
| CLVIII | H | H | 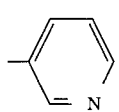 | H | 0.7 (V) | 97 |
| CLIX | H | 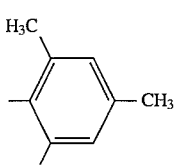 | H | H | 0.66 (III) | 93 |
| CLX | H | 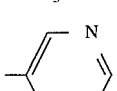 | H | H | 0.72 (III) | 78 |
| CLXI | H | 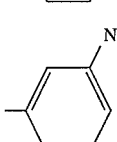 NO₂ | H | H | 0.85 (V) | 95 |

TABLE XVI-continued

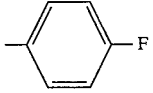

| Ex. No. | V | W | X | Z | $R_f$* | yield (% of theory) |
|---|---|---|---|---|---|---|
| CLXII | H | 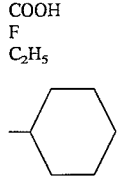 | H | H | 0.87 (V) | 100 |
| CLXIII | H | H | COOH | H | | |
| CLXIV | H | H | F | H | 0.77 (IV) | 77 |
| CLXV | H | H | $C_2H_5$ | H | 0.84 (IV) | 78 |
| CLXVI | H | H | 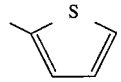 | H | 0.9 (IV) | 65 |
| CLXVII | H | H | $OCH_3$ | H | 0.371 (I) | 92 |
| CLXVIII | $OCH_3$ | H | $OCH_3$ | H | 0.257 | 88.3 |
| CLXIX | H | H | OH | H | 0.27 (IV) | 43 |
| CLXX | H | H | 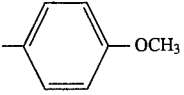 | H | 0.85 (IV) | 80 |
| CLXXI | H | H | $NO_2$ | H | 0.79 (I) | 88 |
| CLXXII | H | H | Br | H | 0.78 (I) | 58 |
| CLXXIII | H | H | $OCH_3$ | H | 0.75 (I) | 93 |
| CLXXIV | Cl | Cl | H | H | 0.79 (I) | 40 |
| CLXXV | H | H | $CH_3$ | H | 0.34 (I) | 76 |
| CLXXVI | H | H | $CF_3$ | H | 0.41 (I) | 97 |
| CLXXVII | H | 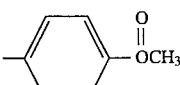 | $NO_2$ | H | 0.53 (I) | 40 |
| CLXXVIII | $CH_3$ | $CH_3$ | H | H | 0.98 (I) | 91 |
| CLXXIX | H | 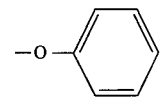 | H | H | 0.53 (I) | 19 |
| CLXXX | H | H | —O—⌬ | H | 0.72 (I) | 78 |

The compounds shown in Tables XVII, XVIII, XIX, XX, XXI and XXII are prepared in analogy to the procedure described in Table VII.

TABLE XVII

| Example No. | V | W | X | Z | A | $R_f$* | yield (% of theory) |
|---|---|---|---|---|---|---|---|
| CLXXXI | H | H | CH₃ | H | cyclopropyl | 0.59 (IV) | 15 |
| CLXXXII | H | CN | H | H | cyclopropyl | 0.5 (IV) | 76 |
| CLXXXIII | H | H | F | H | cyclobutyl | 0.46 (I) | 70 |
| CLXXXIV | H | H | cyclohexyl | H | cyclobutyl | 0.52 (I) | 87 |
| CLXXXV | H | H | cyclohexyl | H | cyclopropyl | 0.55 (I) | 100 |
| CLXXXVI | H | H | F | H | cyclopropyl | 0.5 (I) | 89 |
| CLXXXVII | H | H | NO₂ | H | CH(CH₃)₂ | 0.5 (I) | 30 |
| CLXXXVIII | H | H | CH₃ | H | CH(CH₃)₂ | 0.5 (I) | 77 |
| CLXXXIX | H | OCH₃ | H | H | CH(CH₃)₂ | 0.5 (I) | 65 |
| CIC | Cl | H | Cl | H | CH(CH₃)₂ | 0.53 (I) | 68 |
| CICI | CH₃ | H | CH₃ | H | CH(CH₃)₂ | 0.53 (I) | 86 |
| CICII | H | H | CF₃ | H | CH(CH₃)₂ | 0.53 (I) | 63 |
| CICIII | H | H | CH₃ | H | cyclopropyl | 0.41 (I) | 61 |
| CICIV | H | Br | H | H | OH | 0.69 (IV) | 25 |
| CICV | H | —OCH₃ | H | H | cyclobutyl | 0.48 (I) | 57 |
| CICVI | H | H | CH₃ | H | —OH | 0.53 (V) | 52 |
| CICVII | H | H | CH₃ | H | H | 0.21 (I) | 59 |
| CICVIII | H | OCH₃ | H | H | —C₂H₅ | 0.37 (III) | 44 |
| CICIX | H | OCH₃ | H | H | cyclopropyl | 0.42 (I) | 51 |
| CC | H | H | CH₃ | H | —OC₂H₅ | 0.43 (I) | ~31 |
| CCI | H | CF₃ | H | H | cyclobutyl | 0.55 (I) | 68 |
| CCII | Cl | H | Cl | H | cyclobutyl | 0.54 (I) | 57 |

TABLE XVII-continued

| Example No. | V | W | X | Z | A | $R_f$* | yield (% of theory) |
|---|---|---|---|---|---|---|---|
| CCIII | H | CF$_3$ | H | H |  | 0.41 (I) | 65 |
| CCIV | H | Br | H | H |  | 0.44 (I) | 72 |
| CCV | Cl | H | Cl | H |  | 0.62 (I) | 46 |
| CCVI | H | CH$_3$ | H | H | —C$_2$H$_5$ | 0.51 (I) | 54 |
| CCVII | H | CH$_3$ | H | H |  | 0.53 (I) | 77 |
| CCVIII | H | H | Cl | H | CH$_2$CO$_2$Et | 0.46 (V) | 44 |
| CCIX | —OCH$_3$ | H | OCH$_3$ | H | CH(CH$_3$)$_2$ | 0.08 (III) | 83 |
| CCX | OCH$_3$ | H | OCH$_3$ | H |  | 0.13 (I) | 48.5 |
| CCXI | H | H | OCH$_3$ | H |  | 0.26 (I) | 49.1 |
| CCXII | H | H | Br | H | 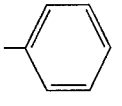 | 0.28 (I) | 13 |
| CCXIII | H | H |  | H |  | 0.44 (I) | 31 |
| CCXIV | H | Br | H | H | C$_2$H$_5$ | 0.3 (III) | 27 |
| CCXV | H | H | CN | H | C$_2$H$_5$ | 0.6 (IV) | 45 |
| CCXVI | H | CN | H | H | C$_2$H$_5$ | 0.6 (IV) | 26 |
| CCXVII | H | H | C$_2$H$_5$ | H | C$_2$H$_5$ | 0.67 (IV) | 58 |
| CCXVIII | H | H | 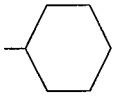 | H | C$_2$H$_5$ | 0.44 (I) | 74 |
| CCXIX | H | H | F | H | C$_2$H$_5$ | 0.07 (III) | 65 |
| CCXX | H | H | Br | H | CH(CH$_3$)$_2$ | 0.3 (I) | 67 |
| CCXXI | H | Br | H | H | CH(CH$_3$) | 0.32 (I) | 31 |
| CCXXII | H | H | CN | H | CH(CH$_3$)$_2$ | 0.65 (IV) | 38 |
| CCXXIII | H | CN | H | H | CH(CH$_3$)$_2$ | 0.63 (IV) | 59 |
| CCXXIV | H | H | C$_2$H$_5$ | H | CH(CH$_3$)$_2$ | 0.2 (III) | 88 |
| CCXXV | H | H |  | H | CH(CH$_3$)$_2$ | 0.2 (III) | 75 |
| CCXXVI | H | H | F | H | CH(CH$_3$)$_2$ | 0.15 (III) | 93 |

TABLE XVII-continued
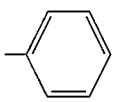
| Example No. | V | W | X | Z | A | $R_f$* | yield (% of theory) |
|---|---|---|---|---|---|---|---|
| CCXXVII | H | H | 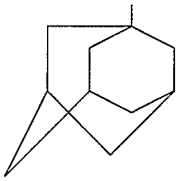 | H | CH(CH$_3$)$_2$ | 0.4 (I) | 86 |
| CCXXVIII | H | H | —(CH$_2$)$_3$CH$_3$ | H | —CH$_2$CO$_2$C$_2$H$_5$ | 0.55 | 68.6 |
| CCXXIX | H | H | C$_6$H$_5$ | H | —CH$_2$CO$_2$C$_2$H$_5$ | 0.358 | 70.6 |
| CCXXX | H | H |  | H | —CHCO$_2$C$_2$H$_5$ | 0.45 | 80.8 |
| CCXXXI | H | H | Br | H | CH$_2$CH$_3$ | 0.133 | 67 |
| CCXXXII | H | H | Ph | H | CH$_2$CH$_3$ | 0.29 | 66 |
| CCXXXIII | H | H | Ph | H | 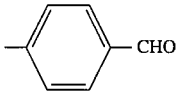 | 0.42 | 31 |
| CCXXXIV | H | H |  | H | 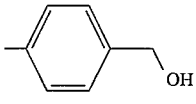 | 0.22 | 28.4 |
| CCXXXV | H | H |  | H | 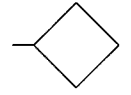 | 0.15 | 89.2 |
| CCXXXVI | H | H | C$_6$H$_5$ | H | 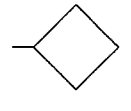 | 0.32 | 70.9 |
| CCXXXVII | H | H | CH$_3$ | H | 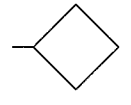 | 0.29 | 58.4 |
| CCXXXVIII | OCH$_3$ | H | CH$_3$ | H | 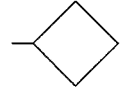 | 0.29 | 67.2 |
| CCXXXIX | H | H | Br | H | 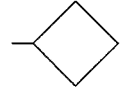 | 0.38 | 77.6 |

TABLE XVIII

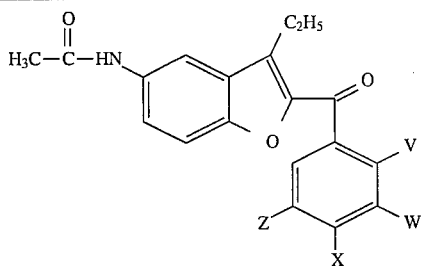

| Example No. | V | W | X | Z | $R_f$* | yield (% of theory) |
|---|---|---|---|---|---|---|
| CCXL | Cl | H | Cl | H | 0.51 (I) | 59 |
| CCXLI | H | $CH_3$ | H | H | 0.60 (I) | 53 |
| CCXLII | H | $OCH_3$ | H | H | 0.43 (I) | 47 |
| CCXLIII | H | $CF_3$ | H | H | 0.53 (I) | 42 |
| CCXLIV | H | $NO_2$ | H | H | 0.42 (I) | 12 |
| CCXLV | H | H | $OCH_3$ | H | 0.58 | 97 |
| CCXLVI | H | H | 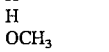 | H | 0.45 | 68 |

TABLE XVIII-continued

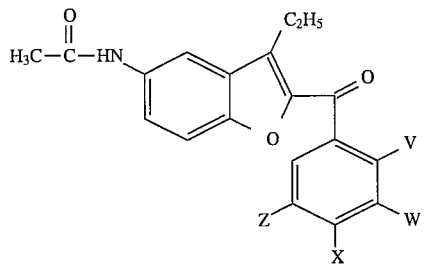

| Example No. | V | W | X | Z | $R_f$* | yield (% of theory) |
|---|---|---|---|---|---|---|
| CCXLVII | H | H | $C_2H_5$ | H | 0.56 (IV) | 63 |
| CCXLVIII | H | H | $CH_3$ | H | 0.27 (I) | 86 |
| CCXLIX | H | H | 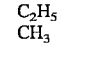 | H | 0.35 (I) | 79 |

TABLE XIX

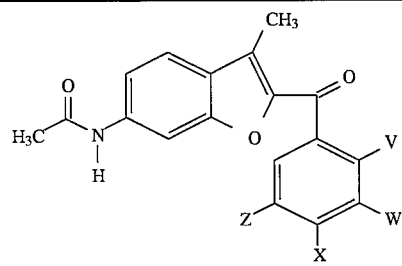

| Example No. | V | W | X | Z | $R_f$* | yield (% of theory) |
|---|---|---|---|---|---|---|
| CCL | H | 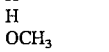 | H | H | 0.39 (I) | 65 |
| CCLI | H | H | $C_9H_{19}$ | H | 0.06 (III) | 57 |
| CCLII | H | H | $C_6H_{13}$ | H | 0.42 (V) | 35 |
| CCLIII | H | H | (3-pyridyl) | H | 0.66 (V) | 67 |
| CCLIV | H | (mesityl) | H | H | 0.48 (V) | 83 |
| CCLV | H | (pyrimidinyl) | H | H | 0.68 (V) | 97 |
| CCLVI | H | H | F | H | 0.8 (I) | 98 |
| CCLVII | H | H | $C_2H_5$ | H | 0.5 (IV) | 50 |

TABLE XIX-continued

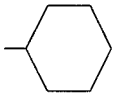

| Example No. | V | W | X | Z | R_f* | yield (% of theory) |
|---|---|---|---|---|---|---|
| CCLVIII | H | H | cyclohexyl | H | 0.6 (IV) | 71 |
| CCLIX | H | H | OCH$_3$ | H | 0.2 (IV) | 63 |
| CCLX | OCH$_3$ | H | OCH$_3$ | H | 0.2 (IV) | 62 |
| CCLXI | CH$_3$ | H | CH$_3$ | H | 0.4 (I) | 51 |
| CCLXII | H | H | -C$_6$H$_4$-COCH$_3$ | H | 0.2 (I) | 21 |
| CCLXIII | H | -O-C$_6$H$_5$ | H | H | 0.32 (I) | 68 |
| CCLXIV | H | H | OH | H | 0.14 (I) | 20 |
| CCLXV | H | H | furyl | H | 0.2 (IV) | 61 |
| CCLXVI | H | H | thienyl | H | 0.47 (IV) | 30 |
| CCLXVII | H | H | Br | H | 0.65 | 60 |
| CCLXVIII | H | H | -C$_6$H$_4$-Cl | H | 0.1 | 76 |

TABLE XX

| Example No. | V | W | X | R_f* | yield (% of theory) |
|---|---|---|---|---|---|
| CCLXIX | H | H | F | 0.5 (IV) | 83 |
| CCLXX | H | H | Br | 0.45 (III) | 68 |
| CCLXXI | H | H | C$_2$H$_5$ | 0.48 (IV) | 60 |

TABLE XX-continued

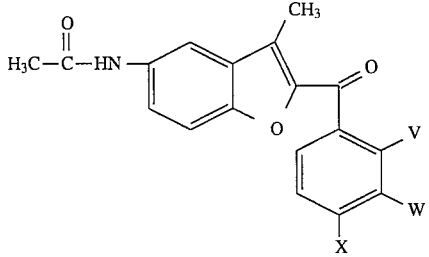

| Example No. | V | W | X | $R_f$* | yield (% of theory) |
|---|---|---|---|---|---|
| CCLXXII | H | H | (cyclohexyl) | 0.54 (IV) | 78 |
| CCLXXIII | H | Br | H | 0.27 (I) | 71 |
| CCLXXIV | Cl | H | Cl | 0.26 (I) | 65 |
| CCLXXV | H | $NO_2$ | H | 0.15 (I) | 20 |
| CCLXXVI | H | $CH_3$ | H | 0.25 (I) | 73 |
| CCLXXVII | $CH_3$ | H | $CH_3$ | 0.36 (I) | 57 |
| CCLXXVIII | H | H | $NO_2$ | 0.19 (I) | 16 |
| CCLXXIX | H | $CF_3$ | H | 0.35 (I) | 37 |
| CCLXXX | H | $OCH_3$ | H | 0.21 (I) | 96 |
| CCLXXXI | H | H | (—C$_6$H$_4$—$OCH_3$) | 0.26 (I) | 81 |

TABLE XXI

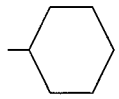

| Example No. | E | X | W | $R_f$* | yield (% of theory) |
|---|---|---|---|---|---|
| CCLXXXII | $COCH_3$ | H | (m-$NO_2$-phenyl) | 0.64 (V) | 55 |
| CCLXXXIII | $COCH_3$ | H | (p-F-phenyl) | 0.75 (V) | 31 |

Preparation Example

EXAMPLE 1

3-[2-(4-Chlorobenzoyl)-6-(2-methoxy-2-oxo-acetamido)-3-benzofuranyl]propanoic acid, methylester

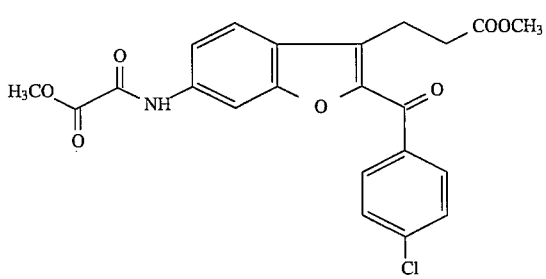

0.5 g (1,4 mmol) of example III were dissolved in 20 ml methylene chloride and 8 ml triethylamine. At 0° C. 0.2 g (1.5 mmol) methyloxalyl-methylester chloride were added dropwise. After warming up to room temperature it was further stirred for 1 h. The solvent was distilled off, the residue solved in ethylacetate and washed three times with water. The organic layer was dried using $Na_2SO_4$ concentrated in vacuo and purified by crystallisation.

Yield: 0.4 g (65%)

$R_f$ (III)=0,22

The compounds shown in Tables XXII and XXIII were prepared in analogy to the procedure of Example 1:

TABLE XXII

| Ex. No. | V | W | X | Z | A | $R_f$* | Yield (% of theory) |
|---|---|---|---|---|---|---|---|
| 2 | H | H | CH$_3$ | H | —CH$_2$CH$_2$COOCH$_3$ | 0.69 (IV) | 16 |
| 3 | H | NO$_2$ | H | H | —CH$_2$CH$_2$COOCH$_3$ | 0.70 (IV) | 12 |
| 4 | H | CH$_3$ | Cl | H | —CH$_2$CH$_2$COOCH$_3$ | 0.73 (I) | 74 |
| 5 | H | H | Cl | H | —COOC$_2$H$_5$ | 0.8 (IV) | 75.5 |
| 6 | H | H | CH$_3$ | H | —CH$_3$ | 0.71 (IV) | 76 |
| 7 | H | H | Cl | H | —CH$_2$CH$_2$COOCH$_3$ | 0.69 (IV) | 5 |
| 8 | H | Cl | H | H | —CH$_2$CH$_2$COOCH$_3$ | 0.57 (I) | 92 |
| 9 | H | OCH$_3$ | H | H | —CH$_2$CH$_2$COOCH$_3$ | 0.50 (I) | 88 |
| 10 | H | H | SCH$_3$ | H | —CH$_2$CH$_2$COOCH$_3$ | 0.38 (I) | 84 |
| 11 | H | H | F | H | —CH$_2$CH$_2$COOCH$_3$ | 0.45 (I) | 95 |
| 12 | H | H | CN | H | —CH$_2$CH$_2$COOCH$_3$ | 0.35 (I) | 88 |
| 13 | Cl | H | Cl | H | —CO$_2$C$_2$H$_5$ | 0.37 (III) | 76.4 |
| 14 | H | H | Cl | H | —OH | 0.63 (V) | 35 |
| 15 | H | CN | H | H | —CH$_2$CH$_2$CO$_2$CH$_3$ | 0.45 (I) | 96 |
| 16 | Cl | H | Cl | H | —CH$_2$CH$_2$CO$_2$CH$_3$ | 0.63 (I) | 82 |
| 17 | H | H | C$_6$H$_5$ | H | —CH$_3$ | 0.45 (I) | 89 |

TABLE XXIII

| Ex. No. | V | W | X | Z | A | R$^3$ | $R_f$* | Yield (% of theory) |
|---|---|---|---|---|---|---|---|---|
| 18 | H | H | CH$_3$ | H | CH$_3$ | —OH | 0.14 (V) | 60 |
| 19 | H | H | CH$_3$ | H | CH$_3$ | —NH$_2$ | 0.41 (IV) | 74 |
| 20 | H | H | CH$_3$ | H | CH$_3$ | —NHC$_2$H$_5$ | 0.67 (IV) | 88 |
| 21 | H | H | Cl | H | CH$_3$ | —OCH$_3$ | 0.14 (III) | 72 |
| 22 | H | H | Cl | H | OH | —OCH$_3$ | 0.34 (V) | 100 |
| 23 | H | H | Cl | H | —CH$_2$CH$_2$COOCH$_3$ | —OCH(CH$_3$)$_2$ | 0.4 (III) | 37 |
| 24 | H | H | Cl | H | —CH$_2$CH$_2$COOCH$_3$ | —OC(CH$_3$)$_3$ | 0.3 (III) | 20 |
| 25 | H | OCH$_3$ | H | H | —CH$_2$CH$_2$CO$_2$CH$_3$ | —OCH$_3$ | 0.38 (I) | 77 |
| 26 | H | Cl | H | H | —CH$_2$CH$_2$CO$_2$CH$_3$ | —OCH$_3$ | 0.43 (I) | 67 |
| 27 | H | CN | H | H | —CH$_2$CH$_2$CO$_2$CH$_3$ | —OCH$_3$ | 0.14 (I) | 67 |

EXAMPLE 28

3-[2-(4-Chloro-benzoyl)-6-(ethoxycarbonecarbonyl-amino)-benzofuran-3-yl]propionic acid

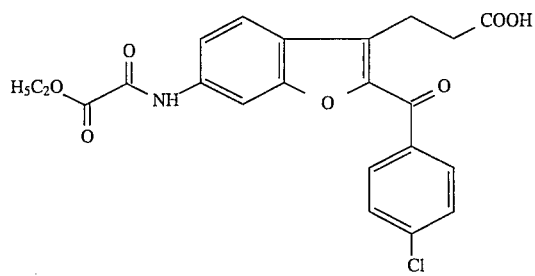

1.5 g (4.2 mmol) of the compound from starting compounds Example III were dissolved in 50 ml methanol/tetrahydrofuran (1:1) and 5.5 ml of a 2N NaOH solution were added. The mixture was stirred at r.t. for 24 hours, disssolved in water and acidified with 1N hydorchloric acid. The precipitate was filtered off, washed several times with water and dried in vacuo. The further reaction was carried out as described in Example 1.

Yield: 0.85 g (46%)

$R_f$: 0.28 (IV)

The compounds shown in table XXIV are prepared in analogy to the procedure of example 28:

EXAMPLE 41

N-[3-(2-Carbamoyl-ethyl)-2-(4-chloro-benzoyl)-benzofuran-6-yl]-oxalamic acid methyl ester

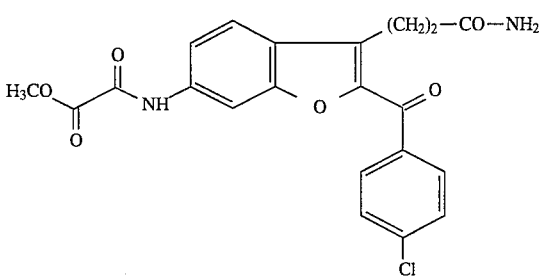

0.56 g (1.3 mmol) of the acid from example 1 were dissolved in 5 ml THF, 0.25 g (1.5 mmol) 1,1'-carbonyl-bis-1H-imidazole were added and the mixture was stirred at room temperature for 12 hours. Subsequently NH$_3$-gas was added for 2 hours using an inlet pipe. After one additional hour stirring at r.t. the solvent was distilled off in vacuo. The residue was taken up in ethylacetate and washed three times with water, one time with a NaHCO$_3$ solution and one time with a NaCl solution. The organic phase was dried using MgSO$_4$ and the solvent was removed in vacuo.

Yield: 83%

$R_f$: 0.62 (V)

TABLE XXIV

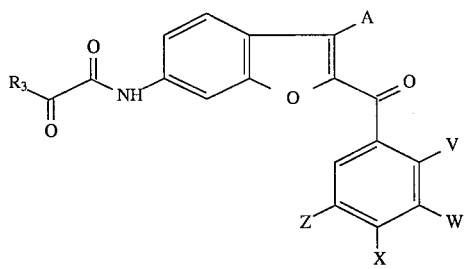

| Ex. No. | V | W | X | Z | A | R$^3$ | R$_f$* | Yield (% of theory) |
|---|---|---|---|---|---|---|---|---|
| 29 | H | H | C$_6$H$_5$ | H | —CH$_3$ | —OH | 0.5 (V) | 78 |
| 30 | H | H | Cl | H | CH$_2$CH$_2$COOH | —OH | 0.1 (V) | 48 |
| 31 | H | H | Cl | H | CH$_2$CH$_2$COONa | —ONa | 0.1 (V) | quant. |
| 32 | H | OCH$_3$ | H | H | CH$_2$CH$_2$CO$_2$H | —OH | 0.05 (V) | 46 |
| 33 | H | H | SCH$_3$ | H | CH$_2$CH$_2$CO$_2$H | —OH | 0.5 (V) | 48 |
| 34 | H | H | F | H | CH$_2$CH$_2$CO$_2$H | —OH | 0.1 (V) | 68 |
| 35 | H | H | CN | H | CH$_2$CH$_2$CO$_2$H | —OH | 0.1 (V) | 82 |
| 36 | H | CN | H | H | CH$_2$CH$_2$CO$_2$H | —OH | 0.26 (IV) | 40 |
| 37 | H | Cl | H | H | CH$_2$CH$_2$CO$_2$H | —OH | | |
| 38 | Cl | H | Cl | H | CH$_2$CH$_2$CO$_2$H | —OH | | |
| 39 | H | Br | H | H | CH$_2$CH$_2$CO$_2$H | —OH | 0.27 (IV) | |
| 40 | H | H | Br | H | CH$_2$CH$_2$CO$_2$H | —OH | 0.31 (IV) | |

The compounds shown in table XXV are prepared in analogy to the procedure of example 41:

TABLE XXV

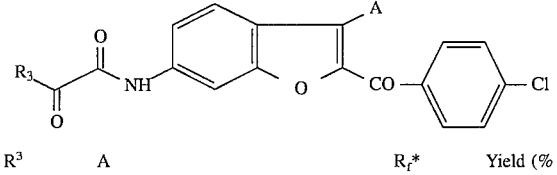

| Ex. No. | R³ | A | $R_f$* | Yield (% of theory) |
|---|---|---|---|---|
| 42 | —OC₂H₅ | —CO—NH—(thiazoline) | 0.36 (I) | 12 |
| 43 | —OC₂H₅ | —CO—NH—CH₂—(phenyl) | 0.39 (I) | 65 |
| 44 | —OC₂H₅ | —CO—NH—(thiazoline) | 0.46 (I) | 7 |
| 45 | —OC₂H₅ | —CO—NH—(lactone) | 0.44 (I) | 11 |

EXAMPLE 46

N-[2-(4-Chloro-benzoyl)-3-(2-cyano-ethyl)-benzofuran-6-yl]-oxalamic acid methyl ester

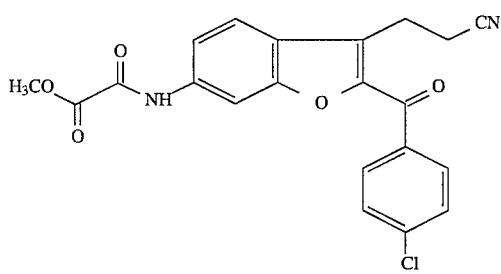

0.56 g (1.3 mmol) of example 41 were dissolved in 15 ml dioxane. 0.2 ml (2.6 mmol) pyridine was added, cooled to 5°–10° C. and 0.22 ml (1.56 mmol) trifluoroacetic anhydride was added dropwise. The mixture was stirred for 3 h at room temperature. The mixture was added to water, washed twice with acethylene chloride. The organic layer was dried and the solvent removed in vacuo.

Yield: 74%
$R_f$: 0.83 (V)

The compounds shown in table XXVI are prepared in analogy to the procedure of example 46:

TABLE XXVI

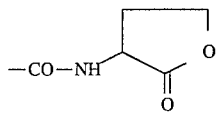

| Ex.-No. | R³ | $R_f$* | Yield (% of theroy) |
|---|---|---|---|
| 47 | —OC₂H₅ | 0.5 (IV) | 77 |
| 48 | —OH | 0.07 (IV) | 80 |

TABLE XXVII

The compounds shown in Table XXVII are prepared in analogy to the procedure of example 1

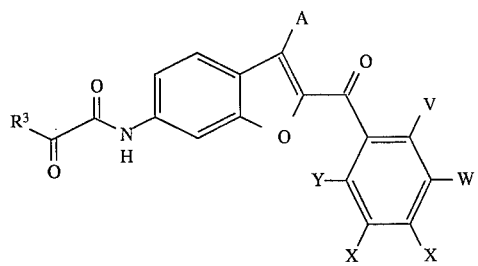

| Example No. | Y | V | W | X | Z | R³ | A | $R_f$* | yield % |
|---|---|---|---|---|---|---|---|---|---|
| 49 | H | H | H | Br | H | —OC₂H₅ | CH₃ | 0.45 (I) | 89 |
| 50 | H | H | Br | H | H | —OC₂H₅ | —CH₂CH₂COOCH₃ | 0.42 (I) | 93 |
| 51 | H | H | H | Br | H | —OC₂H₅ | —CH₂CH₂CO₂CH₃ | | |
| 52 | H | H | H | NO₂ | H | —O—C₂H₅ | —CH₂CH₂—CO₂CH₃ | | |
| 53 | CH₃ | CH₃ | H | CH₃ | H | —O—C₂H₅ | CH₃ | 0.82 (IV) | 90 |
| 54 | H | H | H | NO₂ | H | —OC₂H₅ | CH₃ | 0.48 (III) | 51 |
| 55 | H | H | CN | H | H | —OC₂H₅ | CH₃ | 0.58 (I) | 37 |
| 56 | H | H | H | CN | H | —OC₂H₅ | CH₃ | 0.8 (IV) | 93 |
| 57 | H | H | H | CH₃ | H | —OC₂H₅ | 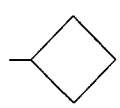 | 0.7 (IV) | 70 |
| 58 | H | H | H | CH₃ | H | —OC₂H₅ | —CH(CH₃)₂ | 0.83 (V) | 92 |
| 59 | H | H | H | CH₃ | H | —OC₂H₅ | —CH₂CH₃ | 0.68 (IV) | 93 |
| 60 | H | H | H | CH₃ | H | —OCH₂CF₃ | —CH₃ | 0.5 (VI) | 3 |
| 61 | H | H | H | C₄H₉ | H | —OC₂H₅ | —CH₂COOC₂H₅ | 0.52 (I) | 99 |
| 62 | H | H | H | C₄H₉ | H | —OCH₃ | —CH₂COOC₂H₅ | 0.37 (I) | 69 |

TABLE XXVIII

The compounds shown in Table XXVIII are prepared in analogy to the procedure of example 28

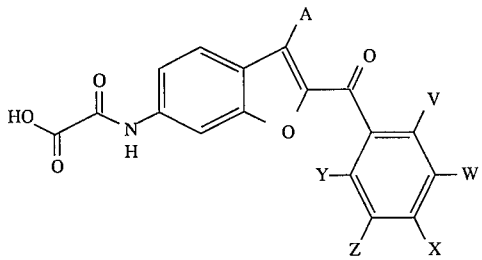

| Example No. | Y | V | W | X | Z | A | $R_f$* | yield % |
|---|---|---|---|---|---|---|---|---|
| 63 | H | H | H | Br | H | —CH₃ | 0.1 (V) | 89 |
| 64 | CH₃ | CH₃ | H | CH₃ | H | —CH₃ | 0.02 (V) | 59 |
| 65 | H | H | CN | H | H | —CH₃ | 0.01 (V) | 65 |
| 66 | H | H | H | NO₂ | H | —CH₂CH₂CO₂H | 0.05 (V) | 40 |
| 67 | H | H | NO₂ | H | H | —CH₂CH₂CO₂ | 0.02 (V) | 40 |
| 68 | H | H | H | NO₂ | H | CH₃ | 0.02 (V) | 80 |
| 69 | H | H | H | CN | H | CH₃ | 0.01 (V) | 80 |
| 70 | H | H | H | CH₃ | H | 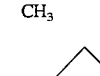 | 0.1 (V) | 70 |
| 71 | H | H | H | CH₃ | H | —CH(CH₃)₂ | 0.04 (V) | 100 |
| 72 | H | H | H | CH₃ | H | —CH₂CH₃ | 0.05 (V) | 90 |

TABLE XXIX

The compounds shown in Table XXIX are prepared in analogy to the procedure of example 1

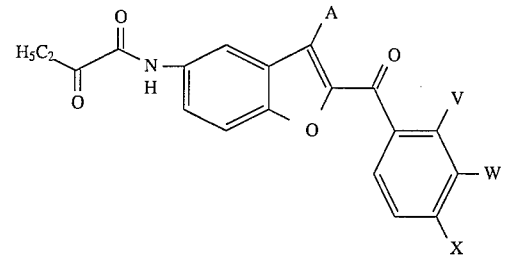

| Example No. | V | W | X | A | $R_f$* | yield % |
|---|---|---|---|---|---|---|
| 75 | H | H | CH₃ | CH₃ | 0.8 ((IV)) | 83 |
| 74 | H | H | H | CH₃ | 0.3 (IV) | 100 |
| 75 | H | H | CN | CH₃ | 0.85 | 89 |

The compounds shown in Table XXX are prepared in analogy to the procedure of example 28

TABLE XXX

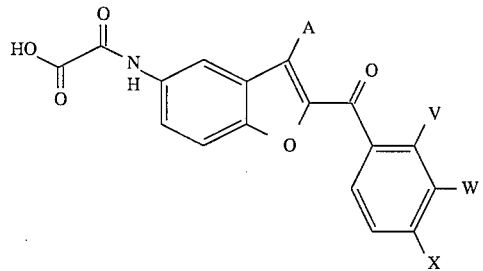

| Example No. | V | W | X | A | $R_f$ | Yield |
|---|---|---|---|---|---|---|
| 76 | H | H | CH₃ | CH₃ | 0.01 (V) | 100 |

TABLE XXX-continued

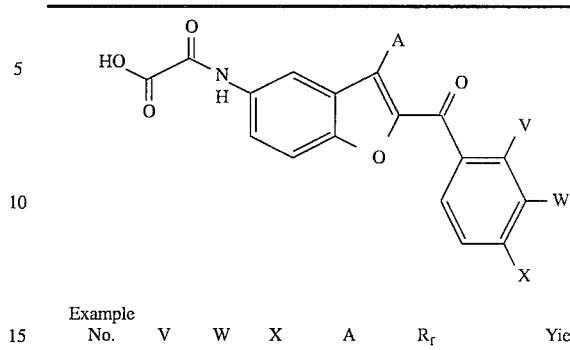

| Example No. | V | W | X | A | $R_f$ | Yield |
|---|---|---|---|---|---|---|
| 77 | H | H | H | CH₃ | 0.02 (V) | 89 |
| 78 | H | H | CN | CH₃ | 0.01 (V) | 93 |

The compounds shown in Table XXXI are prepared in analogy to the procedure of the example 1

TABLE XXXI

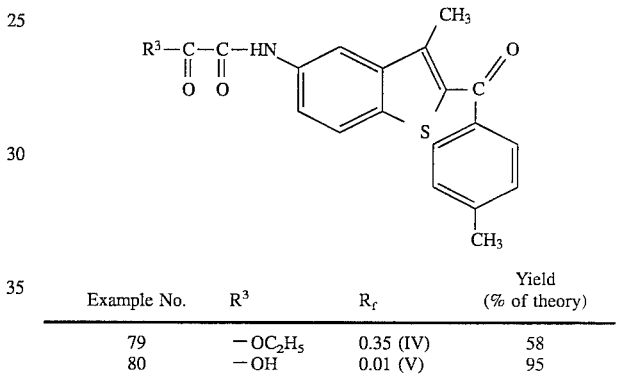

| Example No. | $R^3$ | $R_f$ | Yield (% of theory) |
|---|---|---|---|
| 79 | —OC₂H₅ | 0.35 (IV) | 58 |
| 80 | —OH | 0.01 (V) | 95 |

The compounds shown in Table XXXII are prepared in analogy to the procedure of the example 1.

TABLE XXXII

The compounds shown in Table XXXII are prepared in analogy to the procedure of the example 1.

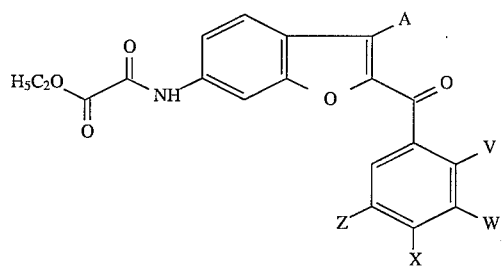

| Ex. No. | V | W | X | Z | A | $R_f$* | Yield (% of theory) |
|---|---|---|---|---|---|---|---|
| 81 | H | H | F | H | CH₃ | 0.75 (IV) | 100 |
| 82 | H | H | C₂H₅ | H | CH₃ | 0.45 (III) | 97 |
| 83 | H | H | —⬡ | H | CH₃ | 0.9 (IV) | 80 |

TABLE XXXII-continued

The compounds shown in Table XXXII are prepared in analogy to the procedure of the example 1.

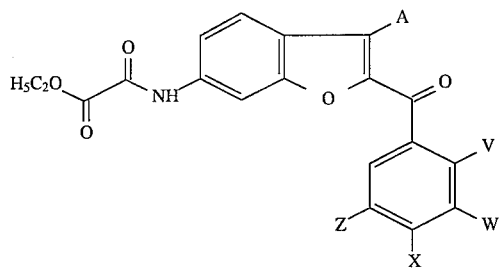

| Ex. No. | V | W | X | Z | A | R_f* | Yield (% of theory) |
|---|---|---|---|---|---|---|---|
| 84 | H | Br | H | H | $C_2H_5$ | 0.5 (III) | 76 |
| 85 | H | H | CN | H | $CH(CH_3)_2$ | 0.65 (I) | 55 |
| 86 | H | CN | H | H | $CH(CH_3)_2$ | 0.7 (I) | 98 |
| 87 | H | H | $C_2H_5$ | H | $CH(CH_3)_2$ | 0.7 (III) | 78 |
| 88 | H | H | cyclohexyl | H | $CH(CH_3)_2$ | 0.7 (I) | 96 |
| 89 | H | H | F | H | $CH(CH_3)_2$ | 0.4 (III) | 48 |
| 90 | H | H | Br | H | $CH(CH_3)_2$ | 0.55 (IV) | 89 |
| 91 | H | Br | H | H | $CH(CH_3)_2$ | 0.58 (III) | 89 |
| 92 | H | H | CN | H | $CH(CH_3)_2$ | 0.72 (I) | 55 |
| 93 | H | CN | H | H | $CH(CH_3)_2$ | 0.7 (I) | 36 |
| 94 | H | H | $C_2H_5$ | H | $CH(CH_3)_2$ | 0.6 (III) | 74 |
| 95 | H | H | cyclohexyl | H | $CH(CH_3)_2$ | 0.62 (III) | 85 |
| 96 | H | H | F | H | $CH(CH_3)_2$ | 0.4 (I) | 72 |
| 97 | H | H | $NO_2$ | H | —$CH_3$ | 0.79 (I) | 83 |
| 98 | H | H | Br | H | —$CH_3$ | 0.83 (I) | 98 |
| 99 | H | H | $OCH_3$ | H | —$CH_3$ | 0.78 (I) | 63 |
| 100 | Cl | Cl | H | H | —$CH_3$ | 0.79 (I) | 82 |
| 101 | H | H | $CH_3$ | H | —$CH_3$ | 0.54 (I) | 89 |
| 102 | H | H | $CF_3$ | H | —$CH_3$ | 0.53 (I) | 51 |
| 103 | H | 4-methoxyphenyl | $NO_2$ | H | —$CH_3$ | 0.76 (I) | 35 |
| 104 | $CH_3$ | $CH_3$ | H | H | —$CH_3$ | 0.73 (I) | 84 |
| 105 | H | 4-acetylphenyl | H | H | —$CH_3$ | 0.6 (I) | 83 |
| 106 | H | phenoxy | H | H | —$CH_3$ | 0.68 (I) | 42 |
| 107 | H | H | $NO_2$ | H | —$CH(CH_3)_2$ | 0.88 (I) | 34 |
| 108 | H | H | $CH_3$ | H | —$CH(CH_3)_2$ | 0.89 (I) | 100 |
| 109 | H | H | $OCH_3$ | H | —$CH(CH_3)_2$ | 0.87 (I) | 41 |
| 110 | Cl | Cl | H | H | —$CH(CH_3)_2$ | 0.37 (I) | 80 |
| 111 | $CH_3$ | $CH_3$ | H | H | —$CH(CH_3)_2$ | 0.34 (I) | 67 |
| 112 | H | H | $CF_3$ | H | —$CH(CH_3)_2$ | 0.81 (I) | 91 |
| 113 | H | $NO_2$ | H | H | $CH_3$ | 0.51 (II) | 51 |
| 114 | H | H | $NO_2$ | H | $CH(CH_3)_2$ | 0.74 (I) | 34 |
| 115 | H | H | OH | H | $CH_3$ | 0.54 (I) | 36 |
| 116 | H | H | $OCOCO_2Et$ | H | $CH_3$ | 0.52 (IV) | 85 |

TABLE XXXII-continued

The compounds shown in Table XXXII are prepared in analogy to the procedure of the example 1.

| Ex. No. | V | W | X | Z | A | $R_f$* | Yield (% of theory) |
|---|---|---|---|---|---|---|---|
| 117 | H | H | furyl (O) | H | CH$_3$ | 0.4 (IV) | 68 |
| 118 | H | H | CH$_3$ | H | cyclopropyl | 0.76 (IV) | 92 |
| 119 | H | H | thienyl (S) | H | CH$_3$ | 0.53 (III) | 5 |
| 120 | H | CN | H | H | cyclopropyl | 0.35 (I) | 37 |
| 121 | H | H | F | H | cyclobutyl | 0.68 (III) | 92 |
| 122 | H | H | cyclohexyl | H | cyclobutyl | 0.46 (III) | 88 |
| 123 | H | H | cyclohexyl | H | cyclopropyl | 0.6 (III) | 67 |
| 124 | H | H | F | H | cyclopropyl | 0.45 (I) | 84 |
| 125 | H | CH$_3$ | H | H | cyclopropyl | 0.7 (I) | 79 |
| 126 | H | —OCH$_3$ | H | H | cyclobutyl | 0.82 (I) | 88 |
| 127 | H | H | CH$_3$ | H | —H | 0.82 (I) | 89 |
| 128 | H | OCH$_3$ | H | H | —C$_2$H$_5$ | 0.71 (I) | 33 |
| 129 | H | OCH$_3$ | H | H | cyclopropyl | 0.79 (I) | 82 |
| 130 | H | H | CH$_3$ | H | —OC$_2$H$_5$ | 0.71 (I) | 79 |
| 131 | H | CF$_3$ | H | H | cyclobutyl | 0.82 (I) | 64 |

TABLE XXXII-continued

The compounds shown in Table XXXII are prepared in analogy to the procedure of the example 1.

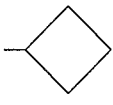

| Ex. No. | V | W | X | Z | A | $R_f$* | Yield (% of theory) |
|---|---|---|---|---|---|---|---|
| 132 | Cl | H | Cl | H |  | 0.75 (I) | 10 |
| 133 | H | CF$_3$ | H | H |  | 0.82 (I) | 89 |
| 134 | H | Br | H | H |  | 0.81 (I) | 85 |
| 135 | Cl | H | Cl | H | 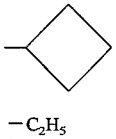 | 0.34 (I) | 86 |
| 136 | H | CH$_3$ | H | H | —C$_2$H$_5$ | 0.63 (I) | 45 |
| 137 | H | CH$_3$ | H | H | 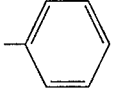 | 0.63 (I) | 60 |
| 138 | H | CF$_3$ | H | H | —C$_2$H$_5$ | 0.58 (I) | 20 |
| 139 | Cl | H | Cl | H | C$_2$H$_5$ | 0.65 (I) | 21 |
| 140 | H | H | CH$_3$ | H | OCH$_3$ |  |  |
| 141 | H | H | C$_4$H$_9$ | H | CH$_2$COOEt | 0.5 (I) | 77 |
| 142 | H | H | naphtyl | H | CH$_2$COOEt | 0.55 (I) | 26 |
| 143 | H | H | 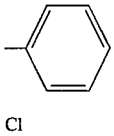 | H | CH$_2$COOEt | 0.5 (I) | 47 |
| 144 | H | H |  | H | C$_2$H$_5$ | 0.4 (I) | 43 |
| 145 | Cl | H | Cl | H | CH$_2$CO$_2$Et | 0.4 (I) | 64 |
| 146 | H | H | Cl | H | CH$_2$CO$_2$Et | 0.44 (I) | 57 |
| 147 | H | H | OCH$_3$ | H | CH(CH$_3$)$_2$ | 0.57 (I) | 85 |
| 148 | OCH$_3$ | H | OCH$_3$ | H | CH(CH$_3$)$_2$ | 0.57 (I) | 59 |
| 149 | H | H | OCH$_3$ | H | C$_2$H$_5$ | 0.5 (I) | 72 |
| 150 | H | H | OCH$_3$ | H | CH$_3$ | 0.47 (I) | 57 |
| 151 | H | H | CH$_3$ | H | CH$_2$COOEt | 0.4 (I) | 70 |
| 152 | OCH$_3$ | H | OCH$_3$ | H | CH$_3$ | 0.3 (I) | 75 |
| 153 | OCH$_3$ | H | OCH$_3$ | H |  | 0.6 (IV) | 37 |
| 154 | H | H | OCH$_3$ | H |  | 0.7 (IV) | 62 |
| 155 | H | H | Br | H |  | 0.5 (IV) | 32 |

TABLE XXXII-continued

The compounds shown in Table XXXII are prepared in analogy to the procedure of the example 1.

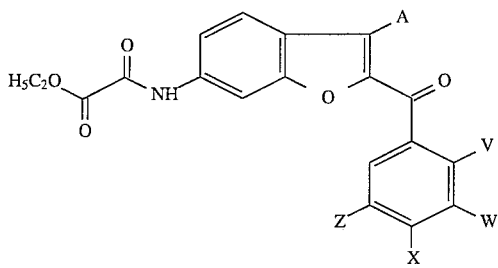

| Ex. No. | V | W | X | Z | A | $R_f$* | Yield (% of theory) |
|---|---|---|---|---|---|---|---|
| 156 | H | H | ⌬ (phenyl) | H | ▷ (cyclopropyl) | 0.56 (IV) | 81 |
| 157 | H | H | CF₃ | H | CH₃ | | |
| 158 | H | H | COOH | H | CH₃ | | |
| 159 | H | —OH | H | H | CH₃ | | |

TABLE XXXIII

The compounds shown in Table XXXIII are prepared in analogy to the procedure of example 28:

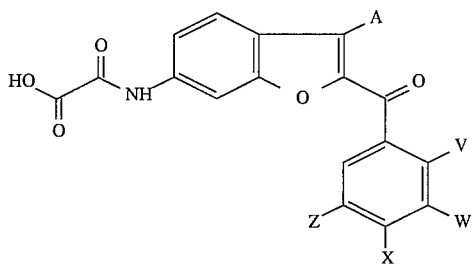

| Ex. No. | V | W | X | Z | A | $R_f$* | Yield (% of theory) |
|---|---|---|---|---|---|---|---|
| 160 | H | H | F | H | CH₃ | 0.01 (IV) | 92 |
| 161 | H | H | C₂H₅ | H | CH₃ | 0.05 (V) | 89 |
| 162 | H | H | phenyl | H | CH₃ | 0.07 (III) | 70 |
| 163 | H | Br | H | H | C₂H₅ | 0.05 (V) | 100 |
| 164 | H | H | CN | H | C₂H₅ | 0.02 (V) | 96 |
| 165 | H | CN | H | H | C₂H₅ | 0.02 (V) | 96 |
| 166 | H | H | C₂H₅ | H | C₂H₅ | 0.08 (III) | 96 |
| 167 | H | H | cyclohexyl | H | C₂H₅ | 0.1 (III) | 88 |
| 168 | H | H | F | H | C₂H₅ | 0 | 87 |
| 169 | H | H | Br | H | CH(CH₃)₂ | 0.06 (V) | 92 |
| 170 | H | Br | H | H | CH(CH₃)₂ | 0.05 (V) | 100 |
| 171 | H | H | CN | H | CH(CH₃)₂ | 0.04 (V) | 62 |
| 172 | H | CN | H | H | CH(CH₃)₂ | 0.04 (V) | 71 |
| 173 | H | H | C₂H₅ | H | CH(CH₃)₂ | 0.08 (III) | 64 |

TABLE XXXIII-continued

The compounds shown in Table XXXIII are prepared in analogy to the procedure of example 28:

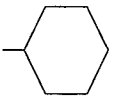

| Ex. No. | V | W | X | Z | A | $R_f$* | Yield (% of theory) |
|---|---|---|---|---|---|---|---|
| 174 | H | H | cyclohexyl | H | $CH(CH_3)_2$ | 0.1 (III) | 87 |
| 175 | H | H | F | H | $CH(CH_3)_2$ | 0 | 91 |
| 176 | H | H | phenyl | H | $C_2H_5$ | 0.2 (V) | 96 |
| 177 | Cl | H | Cl | H | $CH_2CO_2H$ | 0 (V) | 71 |
| 178 | H | H | Cl | H | $CH_2CO_2H$ | 0 (V) | 66 |
| 179 | H | H | $OCH_3$ | H | $CH(CH_3)_2$ | 0.35 (V) | 80 |
| 180 | $OCH_3$ | H | $OCH_3$ | H | $CH(CH_3)_2$ | 0.35 (V) | 73 |
| 181 | H | H | $OCH_3$ | H | $C_2H_5$ | | |
| 182 | H | H | $OCH_3$ | H | $CH_3$ | 0.13 (V) | 92 |
| 183 | H | H | $CH_3$ | H | $CH_2COOH$ | | |
| 184 | $OCH_3$ | H | $OCH_3$ | H | $CH_3$ | 0.2 (I) | 93 |
| 185 | $OCH_3$ | H | $OCH_3$ | H | cyclopropyl | 0.25 (V) | 83 |
| 186 | H | H | $OCH_3$ | H | cyclopropyl | 0.22 (V) | 82 |
| 187 | H | H | Br | H | cyclopropyl | 0.2 (V) | 83 |
| 188 | H | H | phenyl | H | cyclopropyl | 0.28 (V) | quant |
| 189 | H | H | Br | H | $-CH_3$ | 0.07 (V) | 86 |
| 190 | H | $OCH_3$ | H | H | $-CH_3$ | 0.07 (V) | 78 |
| 191 | Cl | H | Cl | H | $-CH_3$ | 0.07 (V) | 79 |
| 192 | H | $CH_3$ | H | H | $-CH_3$ | 0.01 (V) | 100 |
| 193 | H | $CF_3$ | H | H | $-CH_3$ | 0.01 (V) | 75 |
| 194 | H | $NO_2$ | $-C_6H_4-OCH_3$ | H | $-CH_3$ | 0.05 (V) | 100 |
| 195 | $CH_3$ | H | $CH_3$ | H | $-CH_3$ | 0.41 (V) | 75 |
| 196 | H | H | $-C_6H_4-C(O)CH_3$ | H | $-CH_3$ | 0.21 (I) | 91 |
| 197 | H | H | $-O-C_6H_5$ | H | $-CH_3$ | 0.07 | 52 |

TABLE XXXIII-continued

The compounds shown in Table XXXIII are prepared in analogy to the procedure of example 28:

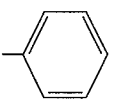

| Ex. No. | V | W | X | Z | A | R$_f$* | Yield (% of theory) |
|---|---|---|---|---|---|---|---|
| 198 | H | NO$_2$ | H | H | —CH(CH$_3$)$_2$ | 0.01 (V) | 100 |
| 199 | H | CH$_3$ | H | H | —CH(CH$_3$)$_2$ | 0.15 (V) | 100 |
| 200 | H | OCH$_3$ | H | H | —CH(CH$_3$)$_2$ | 0.01 (V) | 53 |
| 201 | Cl | H | Cl | H | —CH(CH$_3$)$_2$ | 0.1 (V) | 68 |
| 202 | CH$_3$ | H | CH$_3$ | H | —CH(CH$_3$)$_2$ | 0.14 (V) | 100 |
| 203 | H | CF$_3$ | H | H | —CH(CH$_3$)$_2$ | 0.06 (V) | 64 |
| 204 | H | NO$_2$ | H | H | CH$_3$ | 0.01 (I) | 83 |
| 205 | H | H | NO$_2$ | H | CH$_3$ | 0.33 (V) | 72 |
| 206 | H | NO$_2$ | H | H | CH(CH$_3$)$_2$ | 0.41 (V) | quant. |
| 207 | H | H | H | H | CH$_3$ | 0.07 (V) | 78 |
| 208 | H | H | 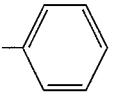 | H | CH$_3$ | 0.06 (IV) | 100 |
| 209 | H | H | 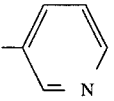 | H | CH(CH$_3$)$_2$ | 0.04 (IV) | 33 |
| 210 | H | H | C$_9$H$_{19}$ | H | CH$_3$ | 0.05 (V) | 100 |
| 211 | H | H | C$_6$H$_{13}$ | H | CH$_3$ | 0.04 (V) | 73 |
| 212 | H | H | 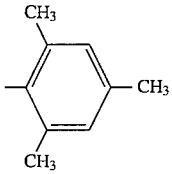 | H | CH$_3$ | 0.07 (V) | 43 |
| 213 | H | 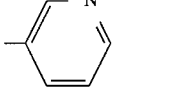 | H | H | CH$_3$ | 0.54 (V) | 75 |
| 214 | H | 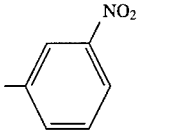 | H | H | CH$_3$ | 0.08 (V) | 68 |
| 215 | H | —OH | H | H | CH$_3$ | | |
| 216 | H | H | COOH | H | CH$_3$ | | |
| 217 | H |  | H | H | CH$_3$ | 0.1 (V) | 49 |
| 218 | H |  | H | H | CH$_3$ | 0.07 (V) | 73 |
| 219 | H | H | OH | H | CH$_3$ | 0.01 (IV) | 57 |

TABLE XXXIII-continued

The compounds shown in Table XXXIII are prepared in analogy to the procedure of example 28:

| Ex. No. | V | W | X | Z | A | $R_f$* | Yield (% of theory) |
|---|---|---|---|---|---|---|---|
| 220 | H | H | furan (O) | H | $CH_3$ | 0.01 (III) | 95 |
| 221 | H | H | $CH_3$ | H | cyclopropyl | 0.01 (V) | 99 |
| 222 | H | H | thiophene (S) | H | $CH_3$ | 0.01 (V) | 10 |
| 223 | H | CN | H | H | cyclopropyl | 0.01 (IV) | 5 |
| 224 | H | H | F | H | cyclobutyl | 0.02 (V) | 98 |
| 225 | H | H | cyclohexyl | H | cyclobutyl | 0.03 (V) | 88 |
| 226 | H | H | cyclohexyl | H | cyclopropyl | 0.01 (IV) | 98 |
| 227 | H | H | F | H | cyclopropyl | 0.01 (V) | 96 |
| 228 | H | $CH_3$ | H | H | cyclopropyl | 0.22 (V) | 100 |
| 229 | H | $-OCH_3$ | H | H | cyclobutyl | 0.44 (V) | 34 |
| 230 | H | H | $CH_3$ | H | $-H$ | 0.11 (V) | 93 |
| 231 | H | $OCH_3$ | H | H | $-C_2H_5$ | 0.25 (V) | 100 |
| 232 | H | $OCH_3$ | H | H | cyclopropyl | 0.34 (V) | 96 |
| 233 | H | H | $CH_3$ | H | $-OC_2H_5$ | 0.05 (V) | 92 |
| 234 | H | $CF_3$ | H | H | cyclobutyl | 0.24 (V) | 75 |
| 235 | Cl | H | Cl | H | cyclobutyl | 0.12 (V) | 89 |

TABLE XXXIII-continued

The compounds shown in Table XXXIII are prepared in analogy to the procedure of example 28:

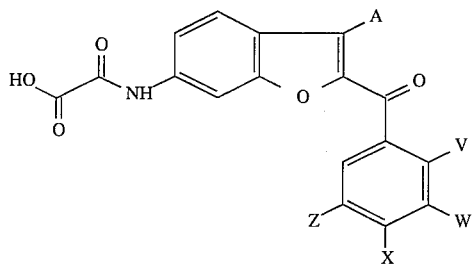

| Ex. No. | V | W | X | Z | A | $R_f$* | Yield (% of theory) |
|---|---|---|---|---|---|---|---|
| 236 | H | CF₃ | H | H | cyclopropyl | 0.12 (V) | 93 |
| 237 | H | Br | H | H | cyclopropyl | 0.22 (V) | 100 |
| 238 | Cl | H | Cl | H | cyclopropyl | 0.20 (V) | 23 |
| 239 | H | CH₃ | H | H | —C₂H₅ | 0.23 (V) | 100 |
| 240 | H | CH₃ | H | H | cyclobutyl | 0.21 (V) | 100 |
| 241 | Cl | H | Cl | H | C₂H₅ | 0.28 (V) | 100 |
| 242 | H | CF₃ | H | H | C₂H₅ | 0.21 (V) | 100 |
| 243 | H | H | CH₃ | H | OCH₃ | | |

The compounds shown in Tables XXXIV, XXXV and XXXVI are prepared in analogy to the procedure of the example 1:

TABLE XXXIV

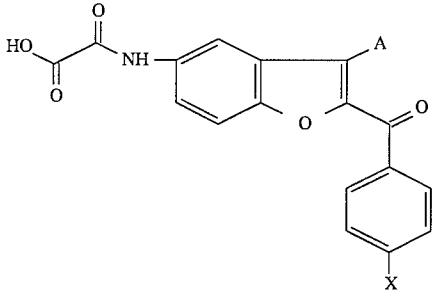

| Ex. No. | X | A | $R_f$* | Yield (% of theory) |
|---|---|---|---|---|
| 244 | F | CH₃ | 0.01 (V) | 93 |
| 245 | Br | CH₃ | 0.05 | 95 |
| 246 | C₂H₅ | CH₃ | 0.03 (V) | 100 |
| 247 | cyclohexyl | CH₃ | 0.06 (V) | 84 |

TABLE XXXV

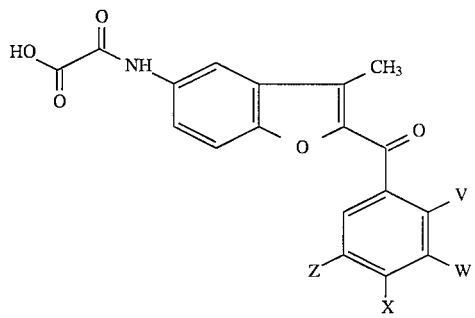

| Ex. No. | V | W | X | Z | $R_f$* | Yield (% of theory) |
|---|---|---|---|---|---|---|
| 248 | Cl | H | Cl | H | 0.21 (V) | 79 |
| 249 | H | NO₂ | H | H | 0.20 (V) | 90 |
| 250 | H | CH₃ | H | H | 0.30 (V) | 75 |
| 251 | CH₃ | H | CH₃ | H | 0.41 (V) | 96 |
| 252 | H | H | NO₂ | H | 0.21 (V) | 76 |
| 253 | H | CF₃ | H | H | 0.6 (V) | 100 |
| 254 | H | OCH₃ | H | H | 0.43 (V) | 72 |
| 255 | H | 4-OCH₃-phenyl | H | H | 0.11 (V) | 95 |

TABLE XXXVI

[Structure: benzofuran with HOOC-C(O)-NH- group at 5-position, C2H5 at 3-position, and C(O)-phenyl(V,W,X,Z) at 2-position]

| Ex. No. | V | W | X | Z | R_f* | Yield (% of theory) |
|---|---|---|---|---|---|---|
| 256 | Cl | H | Cl | H | 0.15 (IV) | quant. |
| 257 | H | CH₃ | H | H | 0.10 (IV) | quant. |
| 258 | H | OCH₃ | H | H | 0.10 (IV) | |
| 259 | H | CF₃ | H | H | 0.15 (IV) | |
| 260 | H | H | OCH₃ | H | 0.10 (V) | 50.6 |
| 261 | H | H | phenyl | H | 0.31 (V) | 89.3 |

TABLE XXXVII

The compounds shown in Table XXXVII are prepared in analogy to the product of example 1:

[Structure: benzofuran with R₃-C(O)-C(O)-NH- group, A substituent at 3-position, and C(O)-phenyl(W,X,Z) at 2-position]

| Ex. No. | W | X | Z | R₃ | A | R_f* | Yield (% of theory) |
|---|---|---|---|---|---|---|---|
| 262 | H | H | H | OC₂H₅ | CH₃ | 0.17 (III) | 71 |
| 263 | H | CH₃ | H | OCH₂OCOCH₃ | CH₃ | 0.05 (III) | 41 |
| 264 | H | CH₃ | H | OCH(CH₃)₂ | CH₃ | 0.33 (III) | 80 |
| 265 | H | CH₃ | H | OCH₃ | CH₃ | 0.12 (III) | 66 |
| 266 | H | CH₃ | H | OC₂H₄OCH₃ | CH₃ | 0.06 (III) | 63 |
| 267 | H | CH₃ | H | OC₆H₁₃ | CH₃ | 0.48 (III) | 82 |
| 268 | phenyl | H | H | OC₂H₅ | CH₃ | 0.65 (I) | 84 |
| 269 | H | phenyl | H | OC₂H₅ | CH(CH₃)₂ | 0.9 (IV) | 100 |
| 270 | H | CH₃ | H | OCH₂CH(CH₃)₂ | CH₃ | 0.4 (III) | 68 |
| 271 | H | CH₃ | H | —OCH₂—phenyl | CH₃ | 0.26 (III) | 63 |

TABLE XXXVII-continued
The compounds shown in Table XXXVII are prepared in analogy to the product of example 1:
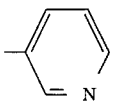
| Ex. No. | W | X | Z | R₃ | A | $R_f$* | Yield (% of theory) |
|---|---|---|---|---|---|---|---|
| 272 | H | $C_9H_{19}$ | H | $OC_2H_5$ | $CH_3$ | 0.22 (III) | 65 |
| 273 | H | $C_6H_{13}$ | H | $OC_2H_5$ | $CH_3$ | 0.06 (II) | 59 |
| 274 | H | 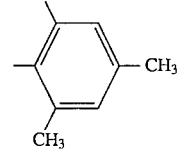 | H | $OC_2H_5$ | $CH_3$ | 0.72 (V) | 97 |
| 275 | 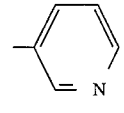 | H | H | $OC_2H_5$ | $CH_3$ | 0.7 (III) | 90 |
| 276 | 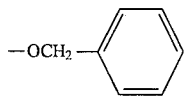 | H | H | $OC_2H_5$ | $CH_3$ | 0.77 (V) | 83 |
| 277 | H | $CH_3$ | H | —OCH₂—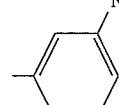 | $CH_2CO_2Et$ | 0.56 (I) | 20 |
| 278 | 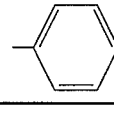 | H | H | $OC_2H_5$ | $CH_3$ | 0.93 (V) | 86 |
| 279 |  | H | H | $OC_2H_5$ | $CH_3$ | 0.9 (V) | 65 |

The compounds shown in Table XXXVIII are prepared in analogy to the procedure of example 1

TABLE XXXVIII

[Structure: benzofuran with H₅C₂O-C(O)-C(O)-NH- substituent, A group at position 3, and C(O)-phenyl-X group]

| Ex. No. | X | A | $R_f$* | Yield (% of theory) |
|---|---|---|---|---|
| 280 | F | CH₃ | 0.3 (III) | 75 |
| 281 | Br | CH₃ | 0.38 (III) | 78 |
| 282 | C₂H₅ | CH₃ | 0.7 (I) | 95 |
| 283 | cyclohexyl | CH₃ | 0.8 (I) | 98 |
| 284 | C₂H₅ | C₂H₅ | 0.65 (I) | 85 |
| 285 | CH₃ | C₂H₅ | 0.63 (III) | 89 |
| 286 | cyclohexyl | C₂H₅ | 0.57 (III) | 89 |

The compounds shown in Table XXXIX are prepared in analogy to the procedure of example 1

TABLE XXXIX

[Structure: benzofuran with H₅C₂O-C(O)-C(O)-NH- substituent, CH₃ at position 3, and C(O)-phenyl with V, W, X substituents]

| Ex. No. | V | W | X | $R_f$* | Yield (% of theory) |
|---|---|---|---|---|---|
| 287 | Cl | H | Cl | 0.71 (I) | 87 |
| 288 | H | NO₂ | H | 0.75 (I) | 90 |
| 289 | H | CH₃ | H | 0.72 (I) | 83 |
| 290 | CH₃ | H | CH₃ | 0.73 (I) | 78 |
| 291 | H | H | NO₂ | 0.72 (I) | 68 |
| 292 | H | CF₃ | H | 0.71 (I) | 79 |
| 293 | H | OCH₃ | H | 0.79 (I) | 82 |
| 294 | H | –C₆H₄–OCH₃ | H | 0.61 (I) | 95 |

The compounds shown in Table XL are prepared in analogy to the procedure of example 1

TABLE XL

[Structure: benzofuran with H₅C₂O-C(O)-C(O)-NH- substituent, C₂H₅ at position 3, and C(O)-phenyl with V, W, X substituents]

| Ex. No. | V | W | X | $R_f$* | Yield (% of theory) |
|---|---|---|---|---|---|
| 295 | Cl | H | Cl | 0.91 (V) | 21 |
| 296 | H | CH₃ | H | 0.62 (I) | 76 |
| 297 | H | OCH₃ | H | 0.68 (I) | 19 |
| 298 | H | CF₃ | H | 0.79 (I) | 78 |
| 299 | H | NO₂ | H | 0.81 (I) | 73 |
| 300 | H | H | phenyl | 0.6 (I) | 56 |

The compounds shown in Tables XLI, XLII, XLIII, XLIV and XLV are prepared in analogy to the procedure of example 1

TABLE XLI

[Structure: benzothiophene with R³-C(O)-C(O)-NH- substituent, CH₃ at position 3, and C(O)-phenyl with W, X substituents]

| Ex. No. | W | X | R³ | $R_f$* | Yield (% of theory) |
|---|---|---|---|---|---|
| 301 | H | H | OEt | 0.82 (I) | 22 |
| 302 | CN | H | OH | 0.01 (I) | 48 |
| 303 | H | H | OCH₃ | 0.6 (V) | 17 |
| 304 | H | CN | OH | 0.02 (I) | 33 |
| 305 | H | F | OEt | 0.8 (I) | 39 |
| 306 | F | H | OEt | 0.77 (I) | 42 |
| 307 | F | H | OH | 0.01 (I) | 96 |
| 308 | CN | H | OEt | 0.78 (I) | 17 |
| 309 | H | F | OH | 0.01 (I) | 97 |
| 310 | H | H | OH | 0.01 (I) | 77 |
| 311 | H | CN | OEt | 0.6 (I) | 3 |

TABLE XLII
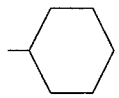
| Ex. No. | A | X | W | R³² | Yield (% of theory) |
|---|---|---|---|---|---|
| 312 | CH₃ | CH₃ | H | Na⁺ | 92 |
| 313 | CH₃ | F | H | Na⁺ | 97 |
| 314 | CH₃ | cyclohexyl | H | Na⁺ | 90 |
| 315 | CH₃ | CH₃ | H | NH₄⁺ | 91 |
| 316 | CH₃ | CH₃ | H | ⊕NH₃—C—(CH₂OH)₃ | 99 |
| 317 | —CH₂CH₃ | F | H | H | 100 |
TABLE XLIII
| Ex. No. | R³³ | A | X | W | Yield (% of theory) | R_f* |
|---|---|---|---|---|---|---|
| 318 | Na⁺ | CH₃ | C₂H₅ | H | 83 | |
| 319 | Na⁺ | CH₃ | cyclohexyl | H | 89 | |
| 320 | ⊕NH₃—C—(CH₂OH)₃ | CH₃ | C₂H₅ | H | 100 | |
| 321 | H | cyclobutyl | H | H | 83 | 0.01 (III) |
| 322 | H | cyclobutyl | Cl | H | 93 | (0.oo5) (III) |
| 323 | H | cyclopropyl | C₂H₅ | H | 95 | 0.01 (III) |

TABLE XLIV

| Ex. No. | $R^{34}$ | A | X | W | Yield (% of theory) | $R_f$* |
|---|---|---|---|---|---|---|
| 324 | Et | cyclobutyl | H | H | 83 | 0.4 (III) |
| 325 | $-CH_2-$ (isopropenyl acetate group) | $CH_3$ | $C_2H_5$ | H | 78 | 0.4 (III) |
| 326 | Et | cyclobutyl | Cl | H | 75 | 0.7 (IV) |
| 327 | $-C_2H_4OC_2H_5$ | $CH_3$ | $CH_3$ | H | 68 | 0.1 (III) |
| 328 | $-CH(CH_3)CH_2OCH_3$ | $CH_3$ | $CH_3$ | H | 33 | 0.06 (III) |
| 329 | $-C_2H_4-{}^{\oplus}N$(morpholinium) | $CH_3$ | $CH_3$ | H | 60 | 0.82 (II) |

TABLE XLV

| Ex. No. | $R^{35}$ | Yield (% of theory) | $R_f$* |
|---|---|---|---|
| 330 | $Na^{(+)}$ | 96.7 | 0.01 (IV) |
| 331 | $K^{(+)}$ | 97.2 | 0.05 (IV) |
| 332 | $^{\oplus}NH_3-C-(CH_2OH)_3$ | 80 | 0.01 (IV) |
| 333 | $-CH_2-O-CO-C(CH_3)_3$ | 65.4 | 0.73 (III) |

The compounds shown in Table XLVI are prepared in analogy to the procedure of example 1

TABLE XLVI

| Ex. No. | $R^3$ | $R_f$* | Yield (% of theory) |
|---|---|---|---|
| 334 | $OC_2H_5$ | 0.34 (III) | 34 |
| 335 | OH | 0.02 (V) | 100 |

The compounds shown in Table XLVII are prepared in analogy to the procedure of example 1

TABLE XLVII

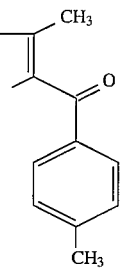

| Ex. No. | X(+) | Yield (% of theory) |
|---------|------|---------------------|
| 336 | $Na^{(+)}$ | 90 |
| 337 | $NH_4^{(+)}$ | 95 |

0.45 g (1.4 mmol) of example LXXIV were dissolved in 20 ml methylenechloride and 8 ml triethylamine. At 0° C. 0.2 g (1.5 mmol) methyloxalyl-methylester chloride were added dropwise. After warming up to room temperature it was further stirred for 1 h. The solvent was distilled off, the residue solved in ethylacetate and washed three times with water. The organic layer was dried using $Na_2SO_4$ concentrated in vacuo and purified by chromatography.

Yield: 0.27 g (48%)

$R_f$=0.13 (I)

The compounds shown in Table XLIX were prepared in analogy to the procedure of Example 343:

TABLE XLVIII

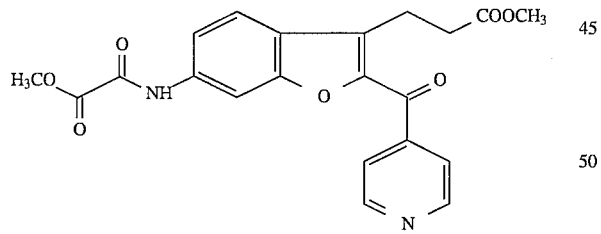

| Ex. No. | A | W | X | $R^{36}$ | $R^{37}$ | Yield (% of theory) | $R_f$* |
|---------|---|---|---|----------|----------|---------------------|--------|
| 338 | $-CH_2-CO_2H$ | H | $CH_3$ | $-NHCO-CO_2H$ | H | 14.6 | 0.44 (V) |
| 339 | $-CH_2-CO_2C_2H_5$ | H | $(CH_2)_3CH_3$ | $-NH-CO-CO_2CH_3$ | H | 68 | 0.366 (I) |
| 340 | $-CH_2-CO_2C_2H_5$ |   | $(CH_2)_3CH_3$ | $-NH-CO-CO_2C_2H_5$ | H | 33 | 0.583 (I) |
| 341 | $-CH_3$ | H | $CH_3$ | $-NH-CO-CO_2H$ | $-CH_3$ |   |   |
| 342 | $-CH_3$ | H | $CH_3$ | $-NH-CO-CO_2C_2H_5$ | $-CH_3$ |   |   |

EXAMPLE 343

3-[6-(Methoxycarbonecarbonyl-amino)-2-(pyridine-4-carbonyl)-3-benzofuranyl]propionic acid, methylester

TABLE XLIX

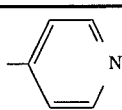

| Ex. No. | R³ | R⁴ | A | $R_f$* | Yield (% of theory) |
|---|---|---|---|---|---|
| 344 | OC₂H₅ | (pyridin-4-yl) | —C₂H₄COOCH₃ | 0.19 (I) | 67 |
| 345 | —OCH₃ | 2,4,6-trimethylpyridin-3-yl | —C₂H₄COOCH₃ | 0.33 (IV) | 41 |
| 346 | OC₂H₅ | (pyridin-3-yl) | —C₂H₄COOCH₃ | 0.36 (I) | 28 |
| 347 | OC₂H₅ | (pyridin-2-yl) | —C₂H₄COOCH₃ | 0.13 (I) | 54 |
| 348 | OC₂H₅ | 2,4,6-trimethylpyridin-3-yl | —CH₃ | 0.53 (IV) | 61 |

EXAMPLE 349

3-[6-(Hydroxycarbonecarbonyl-amino)-2-(pyridin-4-carbonyl)-3-benzofuranyl]propionic acid

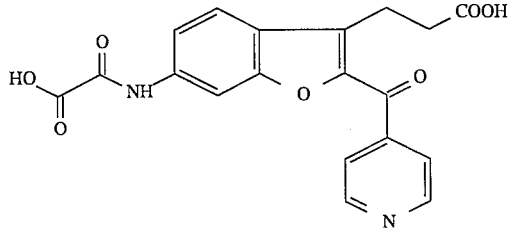

1.5 g (3.5 mmol) of the compound from Example 342 were dissolved in 50 ml methanol/tetrahydrofuran (1:1) and 10 ml of a 2N NaOH solution were added. The mixture was stirred at r.t. for 24 hours, dissolved in water and acidified with 1N hydrochloric acid. The precipitate was filtered off, washed several times with water and dried in vacuo.

Yield: 96%

$R_f$: 0.9 (V)

The compounds shown in Table L to LV are prepared in analogy to the procedure of example 349:

TABLE L

Structure: HO-C(=O)-C(=O)-NH- attached to benzofuran with (CH₂)₂-CO₂H at position 3 and C(=O)-R⁴ at position 2

| Example | R⁴ | $R_f$ | Yield (% of theory) |
|---|---|---|---|
| 350 | 2,4,6-trimethylpyridin-3-yl (H₃C, CH₃, H₃C substituted pyridine) | 0.01 (V) | 64 |
| 351 | pyridin-3-yl | 0.02 (V) | 60 |
| 352 | pyridin-2-yl | 0.01 (V) | 44 |

TABLE LI

Structure: $R^{38}O-C(=O)-C(=O)-NH-$ attached to benzene ring bearing $R^1$, fused to furan with substituent A on one carbon and C=(phenyl with V, W, X substituents) on the other.

| Ex.-No. | $R^{38}$ | $R^1$ | A | V | W | X | $R_f$* | Yield (% of theory) |
|---|---|---|---|---|---|---|---|---|
| 353 | (CH₂)₂OC₂H₅ | H | —CH₃ | H | H | CH₃ | 0.1 (II) | 68 |
| 354 | CH(CH₃)CH₂OCH₃ | H | —CH₃ | H | H | CH₃ | 0.06 (II) | 33 |
| 355 | CH₂CH₂N(piperazine)O—Cl | H | —CH₃ | H | H | CH₃ | 0.82 (V) | 60 |
| 356 | —C₂H₅ | H | —O—CH₃ | H | H | CH₃ | 0.53 (III) | 88 |
| 357 | K⁺ | H | —C₂H₅ | H | H | CH₃ | 0.05 (V) | 92 |
| 358 | —CH₂O—COC(CH₃)₃ | H | —C₂H₅ | H | H | CH₃ | 0.9 (IV) | 74 |
| 359 | —C₂H₅ | Br | H | H | H | CH₃ | 0.38 (IV) | 65 |
| 360 | H | H | cyclobutyl | H | H | OCH₃ | 0.33 (V) | 94 |
| 361 | H | H | cyclobutyl | H | H | phenyl | 0.43 (V) | 90 |
| 362 | H | H | cyclobutyl | OCH₃ | H | OCH₃ | 0.33 (V) | 77 |

TABLE LI-continued

[Structure: R³⁸O-C(=O)-C(=O)-NH-phenyl(R¹)-C(A)=C(-)-C(C)=... with phenyl bearing V, W, X substituents]

| Ex.-No. | R³⁸ | R¹ | A | V | W | X | $R_f$* | Yield (% of theory) |
|---|---|---|---|---|---|---|---|---|
| 363 | H | H | cyclobutyl | H | H | Br | 0.32 (V) | 97 |
| 364 | —C₂H₅ | H | —CH₃ | H | H | N-methylpyrrole-COCOC₂H₅ | 0.5 (I) | 20 |
| 365 | —C₂H₅ | H | —C₂H₅ | H | NO₂ | H | 0.2 (III) | 27 |
| 366 | NH₃C(CH₂OH)₃ | H | cyclopropyl | H | Br | H | 0.05 (V) | 90 |
| 367 | —C₂H₅ | H | —CH₃ | H | H | N-methylpyrrole | 0.6 (I) | 20 |
| 368 | —CH₂CH₂OCH₃ | H | —C₂H₅ | H | H | —CH₃ | 0.48 (III) | 62 |
| 369 | H | H | —CH₃ | H | H | N-methylpyrrole | 0.1 (IV) | 80 |

TABLE LII

[Structure: R³⁵O-C(=O)-C(=O)-NH-phenyl-C(A)=C(-O-)-C(C)=... fused furan with phenyl bearing V, W, X]

| Ex. No. | R³⁹ | A | V | W | X | $R_f$* | Yield (% of theory) |
|---|---|---|---|---|---|---|---|
| 370 | CH₂CH₂N-morpholino | —C₂H₅ | H | H | phenyl | 0.14 (II) | 26 |
| 371 | ⁺NH₃C(CH₂OH)₃ | —C₂H₅ | H | H | —CH₃ | 0.005 (I) | 97 |
| 372 | Na⁺ | —C₂H₅ | H | H | —CH₃ | 0.05 (I) | quant. |
| 373 | NH₄⁺ | —C₂H₅ | H | H | —CH₃ | 0.05 (I) | 57 |
| 374 | —CH₃ | —CH₃ | H | H | —CH₃ | 0.5 (I) | 20 |
| 375 | —CH₂CH₂OCH₃ | —CH₃ | H | H | —CH₃ | 0.4 (I) | 30 |
| 376 | —CH₂CH₂OCH₃ | —C₂H₅ | H | H | —CH₃ | 0.45 (I) | 49.5 |
| 377 | —C₂H | H | H | H | —CH₃ | 0.91 (IV) | 81 |

TABLE LII-continued
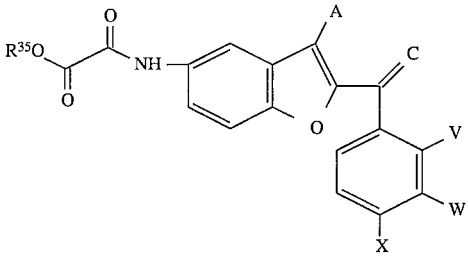
| Ex. No. | R$^{39}$ | A | V | W | X | R$_f$* | Yield (% of theory) |
|---|---|---|---|---|---|---|---|
| 378 | H | H | H | H | —CH$_3$ | 0.28 (IV) | 84 |
TABLE LIII
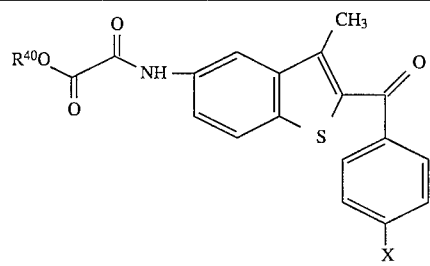
| Ex.-No. | X | R$^{40}$ | R$_f$* | yield (% of theory) |
|---|---|---|---|---|
| 379 | —C(CH$_3$)$_3$ | —C$_2$H$_5$ | 0.7 (IV) | 56 |
| 380 | —C(CH$_3$)$_3$ | H | 0.08 (IV) | quant. |
| 381 | —(CH$_2$)$_3$CH$_3$ | —C$_2$H$_5$ | 0.31 (I) | 48 |
| 382 | Cl | —C$_2$H$_5$ | 0.5 (IV) | 7.5 |
| 383 | Cl | H | 0.08 (IV) | 95 |
TABLE LIV
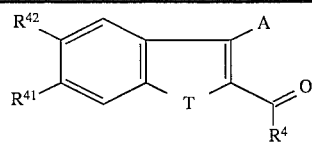
| Ex. No. | R$^{41}$ | R$^{42}$ | A | R$^4$ | T | R$_f$* | yield (% of theory) |
|---|---|---|---|---|---|---|---|
| 384 | 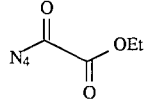 | H | —CH$_2$CO$_2$C$_2$H$_5$ | 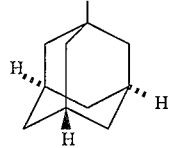 | O | 0.56 (I) | 33 |
| 385 | H |  | —CH$_3$ | (cyclopentyl) | S | 0.19 (2 × II) | 46.9 |
| 386 | H |  | —CH$_3$ | (cyclohexyl) | S | 0.38 (I) | 62.2 |

TABLE LIV-continued
| Ex. No. | R⁴¹ | R⁴² | A | R⁴ | T | R_f* | yield (% of theory) |
|---|---|---|---|---|---|---|---|
| 387 | H |  | —CH₃ |  | S | 0.12 (2 × II) | 5 |
| 388 |  | H | —C₂H₅ |  | O | 0.453 (I) | 24.3 |
| 389 | NH—CO—CO | H |  |  | O | 0.61 (I) | 13 |
TABLE LV
| Ex.-No. | R¹ | R² | A | yield | R_f |
|---|---|---|---|---|---|
| 390 |  | H | CH₃ | 81% | 0.32 (IV) |
| 391 | H |  | CH₃ | 92% | 0.36 (V) |
| 392 | H |  | CH₃ | 74% | 0.01 (V) |
| 393 |  | H | CH₃ | 83% | 0.01 (V) |
| 394 |  | H | C₂H₃ | | |

TABLE LV-continued

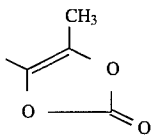

| Ex.-No. | R¹ | R² | A | yield | $R_f$ |
|---|---|---|---|---|---|
| 395 | 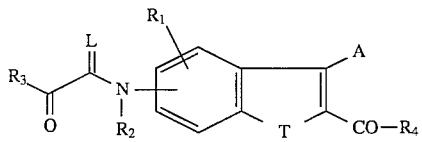 | H | $C_2H_5$ | | |

TABLE LVI

| Example No. | X | A | $R_f$ | Yield (% of theory) |
|---|---|---|---|---|
| 396 | $C_2H_5$ | $C_2H_5$ | 0.01 (IV) | 98 |
| 397 | $CH_3$ | $C_2H_5$ | 0.01 (IV) | 100 |
| 398 | cyclohexyl | $C_2H_5$ | 0.01 (IV) | 95 |

The compounds shown in Table 36 are prepared in analogy to the procedure of example 28.

We claim:

1. An oxalylamino-benzofuran- or benzothienyl-derivative formula in which

L represents an oxygen or sulfur atom, $R^1$ represents hydrogen or straight-chain or branched alkyl having up to 6 carbon atoms or represents halogen, carboxyl, cyano, nitro, trifluoromethyl or a group of a formula —$OR^5$, —$SR^6$ or —$NR^7R^8$, in which $R^5$, $R^6$ and $R^8$ identical or different and denote hydrogen, cycloalkyl having 3 to 6 carbon atoms, benzyl or a 5 to 7-membered saturated or unsaturated heterocycle having up to 3 heteroatoms selected from the group consisting of N, S and O and to which a phenyl ring can be fused and which is optionally substituted by identical or different substituents selected from the group consisting of halogen, cyano, nitro or by a straight-chain or branched alkyl having up to 6 carbon atoms, or denote straight-chain or branched alkyl or alkenyl each having up to 8 carbon atoms, or denote phenyl, which is optionally monosubstituted to disubstituted by identical or different substituents selected from the group consisting of nitro, halogen, carboxy or straight-chain or branched alkoxycarbonyl having up to 6 carbon atoms, or $R^5$ denotes a hydroxyl protecting group, and $R^7$ denotes hydrogen or a straight-chain or branched alkyl having up to 4 carbon atoms $R^2$ represents hydrogen or straight-chain or branched alkyl having up to 6 carbon atoms, $R^3$ represents hydroxyl, benzyloxy or straight-chain or branched alkyl or alkoxy each having up to 10 carbon atoms, and each of which is optionally monosubstituted to trisubstituted by identical or different substituents selected from the group consisting of halogen, carboxyl, trifluoromethyl, phenyl, cyano, or straight-chain or branched alkoxy or oxyacyl each having up to 6 carbon atoms, morpholinyl or by a residue of a formula or represents aryl having 6 to 10 carbon atoms, which is optionally monosubstituted to trisubstituted by identical or different substituents selected from the group consisting of halogen, cyano, nitro, carboxyl, straight-chain or branched alkyl, alkoxy, alkoxycarbonyl or acyl each having up to 6 carbon atoms, or represents a group of a formula —$NR^9R^{10}$, in which $R^9$ and $R^{10}$ are identical or different and denote hydrogen, cycloalkyl having 3 to 6 carbon atoms or denote straight-chain or branched alkyl having up to 8 carbon atoms, which is optionally monosubstituted to trisubstituted by identical or different substituents selected from the group consisting of carboxy, straight-chain or branched alkoxy, alkoxycarbonyl or acyl each having up to 6 carbon atoms or phenyl, or denote aryl having 6 to 10 carbon atoms, which is optionally monosubstituted to trisubstituted by identical or different substituents selected from the group consisting of halogen, cyano, nitro, carboxy, straight-chain or branched alkyl, alkoxy, alkoxycarbonyl or acyl each having up to 6 carbon atoms, or denote a group of a formula —SO$_2$R$^{11}$, in which R$^{11}$ denotes straight-chain or branched alkyl having up to 6 carbon atoms, which is optionally substituted by phenyl, or denotes phenyl, which is optionally substituted by trifluoromethyl, cyano, nitro or straight-chain or branched alkyl having up to 6 carbon atoms, or R$^3$ represents a residue of a formula

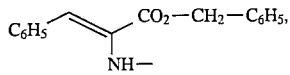

T represents an oxygen or sulfur atom,

A represents hydrogen, hydroxyl, cycloalkyl having up to 6 carbon atoms, carboxy or straight-chain or branched alkoxy or alkoxycarbonyl each having up to 6 carbon atoms, or represents straight-chain or branched alkyl or alkenyl each having up to 8 carbon atoms and each of which is optionally monosubstituted by cyano or by a 5 to 7-membered saturated or unsaturated heterocycle having up to 4 heteroatoms selected from the group consisting of N, S and O, which is optionally substituted by identical or different substituents selected from the group consisting of hydroxy, halogen, cyano, nitro or by a straight-chain or branched alkyl having up to 6 carbon atoms, or alkyl and/or alkenyl are optionally substituted by a group of a formula

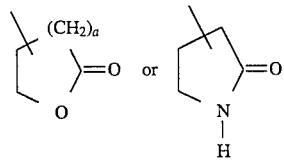

in which
denotes a number 1 or 2, and in which both rings are optionally monosubstituted by hydroxy, halogen or by straight-chain or branched alkyl having up to 6 carbon atoms, or alkyl and/or alkenyl are optionally monosubstituted by a group of a formula —CO—R$^{12}$, —CO—NR$^{13}$R$^{14}$, —CONR$^{15}$—SO$_2$—R$^{16}$ or —PO(OR$^{17}$)(OR$^{18}$), —OR$^{19}$ or

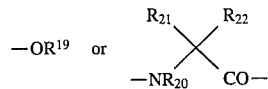

in which

R$^{12}$ denotes hydroxyl, cycloalkyloxy having up 3 to 7 carbon atoms or straight-chain or branched alkyl or alkoxy each having up to 8 carbon atoms, R$^{13}$, R$^{14}$ and R$^{15}$ are identical or different and represent hydrogen, a straight-chain or branched alkyl having up to 6 carbon atoms, phenyl or benzyl, or R$^{13}$ denotes hydrogen, and R$^{14}$ denotes a 5- 7-membered saturated or unsaturated heterocycle having up to 3 heteroatoms from the group consisting of N, S and O, hydroxyl or a residue of the formula

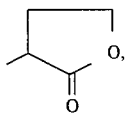

or

R$^{13}$ and R$^{15}$ together with the nitrogen atom form a 5- or 6-membered saturated heterocycle, R$^{16}$ denotes a straight-chain or branched alkyl having up to 6 carbon atoms, which is optionally substituted by phenyl or trifluoromethyl, or denotes phenyl, which is optionally substituted by substituents from the series comprising halogen, cyano, nitro or by a straight-chain or branched alkyl having up to 6 carbon atoms, R$^{17}$, R$^{18}$ and R$^{19}$ are identical or different and represent hydrogen or straight-chain or branched alkyl having up to 6 carbon atoms, R$^{20}$ denotes hydrogen, an aminoprotecting group or straight-chain or branched alkyl having up to 6 carbon atoms, R$^{21}$ and R$^{22}$ are identical or different and denote hydrogen or straight-chain or branched alkyl having up to 4 carbon atoms, or R$^{21}$ has the abovementioned meaning, and R$^{22}$ denotes cycloalkyl having 3 to 6 carbon atoms or aryl having up 6 to 10 carbon atoms or straight-chain or branched alkyl having up to 8 carbon atoms, which is optionally substituted by cyano, methylthio, hydroxy, mercapto, guanidyl or a group of a formula —NR$^{23}$R$^{24}$ or R$^{25}$—CO—, wherein R$^{23}$ and R$^{24}$ have the meaning shown above for R$^{13}$, R$^{14}$ and R$^{15}$ and are identical to the latter or different from the latter, R$^{25}$ denotes hydroxyl, benzyloxycarbonyl, straight-chain or branched alkoxy having up to 6 carbon atoms or the abovementioned group —NR$^{23}$R$^{24}$, or alkyl is optionally substituted by cycloalkyl having 3 to 6 carbon atoms, or by aryl having 6 to 10 carbon atoms, which is optionally substituted by hydroxyl, halogen, nitro, straight-chain or branched alkoxy having up to 8 carbon atoms or by the abovementioned group of the formula —NR$^{23}$R$^{24}$, or alkyl is optionally substituted by indolyl or by a 5 to 6 membered unsaturated heterocycle having up to 3N-atoms wherein optionally all —NH-functions are protected by straight-chain or branched alkyl having up to 6 carbon atoms or by an amino protecting group, or A represents a group of the formula —CONR$^{13'}$R$^{14'}$, in which R$^{13'}$ and R$^{14'}$ are identical or different and have the abovementioned meaning of R$^{13}$ and R$^{14}$, and R$^4$ represents phenyl, or represents a 5 to 7 membered, saturated or unsaturated heterocycle, which can contain up to 4 oxygen, sulphur and/or nitrogen atoms as heteroatoms and to which further a benzene ring can be fused and wherein all rings are optionally monosubstituted to trisubstituted by identical or different substituents selected from the group consisting of hydroxyl, naphthyl, adamantyl, thiophenyl, cycloalkyl having up to 3 to 6 carbon atoms, halogen, nitro, tetrazolyl, thiazolyl, thienyl, furanyl, pyridyl, trifluoromethyl, phenoxy, difluoromethyl, cyano, carboxy, straight-chain or branched alkyl, alkoxy, alkoxycarbonyl or acyl each having up to 11 carbon atoms or by a group of formula—NR$^{26}$R$^{27}$, —SR$^{28}$, SO$_2$R$^{29}$, —O—SO$_2$R$^{30}$, —(CH$_2$)$_b$—O—CO—R$^{31}$,

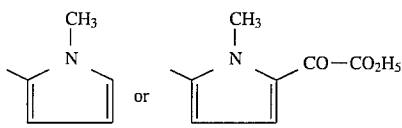 or 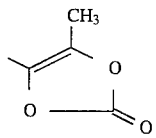

in which
R²⁶ and R²⁷ have the meaning shown above for R⁹ and R¹⁰ and are identical to the latter or different from the latter, or R²⁶ denotes hydrogen, and R²⁷ denotes straight-chain or branched acyl having up to 6 carbon atoms, R²⁸ denotes straight-chain or branched alkyl having up to 6 carbon atoms, R²⁹ and R³⁰ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, R³¹ denotes straight-chain or branched alkoxycarbonyl or alkyl having up to 6 C-atoms or carboxyl, b denotes a number 0 or 1, or phenyl is optionally substituted by phenyl or phenoxy, which are optionally monosubstituted to trisubstituted by halogen, formyl, nitro, straight-chain or branched alkyl, acyl, hydroxyalkyl, alkoxy or alkoxycarbonyl each having up to 6 C-atoms, or R⁴ represents adamantyl, cycloalkyl or cycloalkenyl each having up to 6 carbon atoms, or a salt thereof.

2. An oxalylamino-benzofuran- or benzothienyl-derivative according to claim 1, wherein L represents an oxygen or sulfur atom, R¹ represents hydrogen, straight-chain or branched fluorine, chlorine, bromine, nitro, trifluoromethyl or a group of a formula —OR⁵, —SR⁶ or —NR⁷R⁸, in which R⁷ denotes hydrogen or a straight-chain or branched alkyl having up to 3 carbon atoms, R⁵, R⁶, R⁸ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents selected from the group consisting of fluorine, chlorine, bromine, iodine, cyano, nitro or by a straight-chain or branched alkyl having up to 5 carbon atoms, denote straight-chain or branched alkyl or alkenyl each having up to 6 carbon atoms, or denote phenyl, which is optionally monosubstituted to disubstituted by identical or different substituents selected from the consisting of nitro, fluorine, chlorine, bromine, iodine, carboxy or straight-chain or branched alkoxycarbonyl having up to 5 carbon atoms, or R⁵ denotes benzyl, acetyl or tetrahydropyranyl, R² represents hydrogen or straight-chain or branched alkyl having up to 4 carbon atoms, R³ represents hydroxyl, benzyloxy or straight-chain or branched alkyl or alkoxy each having up to 8 carbon atoms, and each of which is optionally monosubstituted to disubstituted by identical or different substituents selected from the group consisting of fluorine, chlorine, bromine, carboxyl, trifluoromethyl, phenyl, cyano, straight-chain or branched oxyacyl or alkoxy each having up to 4 carbon atoms, morpholinyl or by a residue of a formula

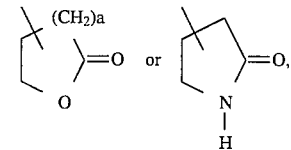

or represents phenyl, which is optionally monosubstituted by substituents from the series comprising fluorine, chlorine, bromine, iodine, cyano, nitro, carboxyl or by a straight-chain or branched alkyl, alkoxy or alkoxycarbonyl each having up to 5 carbon atoms, or represents a group of a formula —NR⁹R¹⁰ in which R⁹ and R¹⁰ are identical or different and denote hydrogen, cyclopropyl, cyclopentyl, cyclohexyl, or denote straight-chain or branched alkyl having up to 6 carbon atoms, which is optionally monosubstituted to trisubstituted by identical or different substituents selected from the group consisting of carboxy, straight-chain or branched alkoxy, alkoxy-carbonyl or acyl each having up to 5 carbon atoms or phenyl, or denote phenyl, which is optionally monosubstituted to trisubstituted by identical or different substituents selected from the group consisting of fluorine, chlorine, bromine, iodine, carboxy, cyano, nitro or by a straight-chain or branched alkyl, alkoxy or alkoxycarbonyl each having up to 5 carbon atoms, or denote a group of a formula —SO₂R¹¹ in which

R¹¹ denotes straight-chain or branched alkyl having up to 4 carbon atoms, which is optionally substituted by phenyl, or denotes phenyl, which is optionally substituted by trifluoromethyl, cyano, nitro or straight-chain or branched alkyl having up to 4 carbon atoms, or R³ represents a residue of a formula

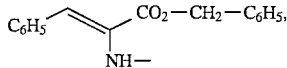

T represents an oxygen or sulfur atom,

A represents hydrogen, cyclopropyl, cyclobutyl, cyclopentyl, hydroxyl, carboxy or straight-chain or a branched alkoxy or alkoxycarbonyl each having up to 5 carbon atoms, or straight-chain or branched alkyl or alkenyl each having up to 6 carbon atoms and each of which is optionally monosubstituted by cyano, tetrazolyl, oxazolyl, oxazolinyl, thiazolyl or a group of a formula in which a denotes a number 1 or 2, and in which all rings are optionally monosubstituted by hydroxy, fluorine, bromine, chlorine or by straight-chain or branched alkyl having up to 4 carbon atoms, or alkyl or alkenyl are optionally monosubstituted by a group of a formula —CO—R¹², —CO—NR¹³R¹⁴, —CONR¹⁵—SO₂—R¹⁶, —PO(OR¹⁷)(OR¹⁸) or —OR¹⁹, in which R¹² denotes hydroxyl, cyclopropyloxy, cyclopentyloxy, cyclohexyloxy or straight-chain or branched alkyl or alkoxy each having up to 6 carbon atoms, $R^{13}$, $R^{14}$ and $R^{15}$ are identical or different and represent hydrogen, straight-chain or branched alkyl having up to 4 carbon atoms, phenyl or benzyl, or $R^{13}$ denotes hydrogen, and $R^{14}$ denotes hydroxyl, thiazolyl, dihydrothiazolyl or a residue of the formula

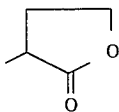

or $R^{13}$ and $R^{14}$ together with the nitrogen atom form a pyrrolidinyl, morpholinyl or a piperidinyl ring, $R^{16}$ denotes a straight-chain or branched alkyl having up to 5 carbon atoms, which is optionally substituted by phenyl or trifluoromethyl, or denotes phenyl, which is optionally substituted by substituents selected from the group consisting of fluorine, chlorine, bromine, iodine, cyano, nitro or by straight-chain or branched alkyl having up to 4 carbon atoms, $R^{17}$, $R^{18}$ and $R^{19}$ are identical or different and represent hydrogen or straight-chain or branched alkyl having up to 6 carbon atoms, or A represents a group —$CONR^{13'}R^{14'}$, in which $R^{13'}$ and $R^{14'}$ have the abovementioned meaning of $R^{13}$ and $R^{14}$ and are identical or different to the latter, and $R^4$ represents phenyl, or represents pyridyl, imidazolyl, pyrazolyl, thienyl, isothiazolyl, 1,3-thiazolyl or benzo[b]thiophenyl, where in all rings are optionally monosubstituted to trisubstituted by identical or different substituents selected from the group consisting of hydroxyl, naphthyl, adamantyl, phenoxy thiophenyl, thienyl, cyclopentyl, cyclohexyl, fluorine, chlorine, bromine, iodine, nitro, tetrazolyl, thiazolyl, furanyl, pyridyl, trifluoromethyl, difluoromethyl, cyano, carboxy, straight-chain or branched alkyl, alkoxy, alkoxycarbonyl or acyl each having up to 10 carbon atoms or by a group of formulae —$NR^{26}R^{27}$, —$SR^{28}$, $SO_2R^{29}$, —O—$SO_2R^{30}$, —$(CH_2)_b$—O—CO—$R^{31}$,

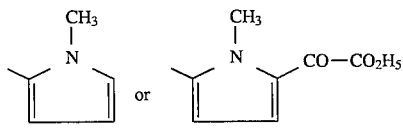

in which $R^{26}$ and $R^{27}$ have the meaning shown above for $R^9$ and $R^{10}$ and are identical to the latter or different from the latter, or $R^{26}$ denotes hydrogen, and $R^{27}$ denotes straight-chain or branched acyl having up to 6 carbon atoms, $R^{28}$ denotes straight-chain or branched alkyl having up to 4 carbon atoms, $R^{29}$ and $R^{30}$ are identical or different and represent straight-chain or branched alkyl having up to 5 carbon atoms or phenyl, which is optionally substituted by trifluoromethyl, fluorine, chlorine, bromine or straight-chain or branched alkyl having up to 3 carbon atoms, $R^{31}$ denotes straight-chain or branched alkoxycarbonyl or alkyl each having up to 4 carbon atoms or carbonyl, b denotes a number 0 or 1, phenyl is optionally substituted by phenyl or phenoxy, which are optionally monosubstituted to trisubstituted by fluorine, chlorine or bromine, formyl, nitro, straight-chain or branched acyl, alkyl, hydroxyalkyl, alkoxy, alkoxycarbonyl each having up to 4 carbon atoms, or $R^4$ represents adamantyl, cyclopropyl, cyclopentyl, cyclohexyl, cyclopentenyl or cyclohexenyl, or a salt thereof.

3. An oxalylamino-benzofuran- or benzothienyl-derivative according to claim 1, wherein L represents an oxygen or sulfur atom, $R^1$ represents hydrogen, straight-chain or branched alkyl having up to 3 carbon atoms, fluorine, chlorine, bromine, nitro, trifluoromethyl or a group of a formula —$OR^5$, in which $R^5$ denotes hydrogen, benzyl, acetyl or denotes straight-chain or branched alkyl each having up to 3 carbon atoms, or denotes phenyl, $R^2$ represents hydrogen or straight-chain or branched alkyl having up to 3 carbon atoms, $R^3$ represents hydroxyl, benzyloxy or straight-chain or branched alkyl or alkoxy each having up to 7 carbon atoms, which is optionally substituted by substituents selected from the group consisting of fluorine, chlorine, bromine, trifluoromethyl, carboxyl, phenyl, cyano, straight-chain or branched alkoxy or oxyacyl each having up to 5 carbon atoms, morpholinyl or by a residue of a formula

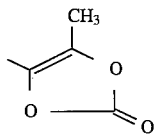

or represents phenyl, which is optionally monosubstituted by different substituents selected from the group consisting of fluorine, chlorine or bromine, or represents a group of a formula —$NR^9R^{10}$, in which $R^9$ and $R^{10}$ are identical or different and denote hydrogen, cyclopropyl, cyclopentyl, cyclohexyl or denote straight-chain or branched alkyl having up to 4 carbon atoms or denote phenyl, or $R^3$ represents a residue of a formula

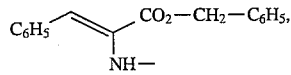

T represents an oxygen atom or sulfur,

A represents hydrogen, cyclopropyl, cyclobutyl, cyclopentyl, hydroxyl, carboxy, or straight-chain or a branched alkoxy or alkoxycarbonyl each having up to 4 carbon atoms, or straight-chain or branched alkyl or alkenyl each having up to 5 carbon atoms and each of which is optionally monosubstituted by cyano, tetrazolyl, oxazolyl, oxazolinyl, thiazolyl or a group of the formula

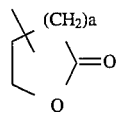

in which a denotes a number 1 or 2, or alkyl or alkenyl are optionally monosubstituted by a group of a formula —CO—$R^{12}$, —CO—$NR^{13}R^{14}$ or —$OR^{19}$, in which $R^{12}$ denotes hydroxyl, cyclopropyloxy, cyclopentyloxy, cyclohexyloxy or straight-chain or branched alkyl or alkoxy each having up to 5 carbon atoms, $R^{13}$ and $R^{14}$ are identical or different and represent hydrogen, straight-chain or branched alkyl having up to 3 carbon atoms, phenyl or benzyl, or $R^{13}$ denotes hydrogen, and $R^{14}$ denotes hydroxyl, thiazolyl, dihydrothiazolyl or a residue of the formula

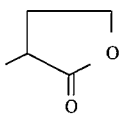

or $R^{13}$ and $R^{14}$ together with the nitrogen atom form a pyrrolidinyl, morpholinyl or piperidinyl ring, $R^{19}$ denotes hydrogen or straight-chain or branched alkyl having up to 4 carbon atoms, A represents a group of the formula $-CONR^{13'}R^{14'}$, in which $R^{13'}$ and $R^{14'}$ have the abovementioned meaning of $R^{13}$ and $R^{14}$ and are identical or different to the latter, and $R^4$ represents phenyl, or represents pyridyl, thienyl, furyl which are optionally monosubstituted to trisubstituted by identical or different substituents selected from the group consisting of hydroxyl, naphthyl, adamantyl, thiopenyl, cyclopentyl, cyclohexy, fluorine, chlorine, bromine, nitro, tetrazolyl, thiazolyl, thienyl, furanyl, pyridyl, phenoxy, trifluoromethyl, difluoromethyl, cyano, carboxyl, straight-chain or branched alkyl, alkoxy, alkoxycarbonyl or acyl each having up to 9 carbon atoms or by a group of formulae $-NR^{26}R^{27}$, $SR^{28}$ or $-(CH_2)_b-O-CO-R^{31}$,

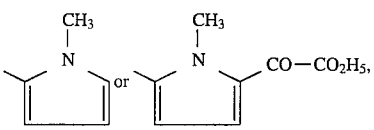

in which $R^{26}$ and $R^{27}$ have the meaning shown above for $R^9$ and $R^{10}$ and are identical to the latter or different from the latter, or $R^{26}$ denotes hydrogen, and $R^{27}$ denotes straight-chain or branched acyl having up to 5 carbon atoms, $R^{28}$ denotes straight-chain or branched alkyl having up to 4 carbon atoms, $R^{31}$ denotes straight-chain or branched alkoxycarbonyl or alkyl each having up to 4 carbon atoms or carboxy, b denotes a number 0 or 1, or phenyl is optionally substituted by phenyl or phenoxy, which are optionally monosubstituted to trisubstituted by fluorine, chlorine, bromine, nitro, formyl or straight-chain or branched acyl, alkoxy, alkyl, hydroxyalkyl or alkoxycarbonyl, each having up to 3 carbon atoms, or $R^4$ represents adamantyl, cyclopentyl, cyclohexyl, cyclopentenyl or cyclohexenyl or a salt thereof.

4. A compound according to claim 1 wherein such compound is N-[3-methyl-2-(4-methyl-benzoyl)-benzofuran-6-yl]-oxalamic acid ethyl ester of the formula

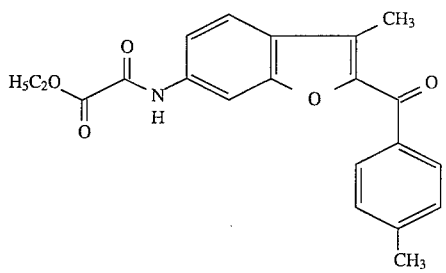

or a salt thereof.

5. A compound according to claim 1 wherein such compound is N-[2-(biphenyl-4-carbonyl)- 3-methyl-benzofuran-6-yl]-oxalamic acid of the formula

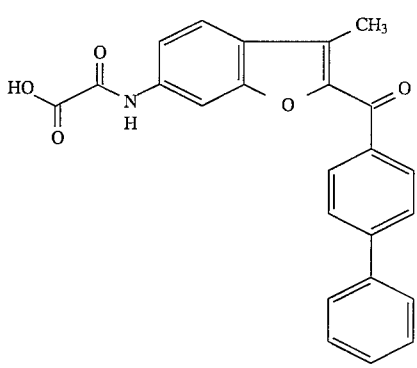

or a salt thereof.

6. A compound according to claim 1 wherein such compound is N-[3-methyl-2-(4-methyl-benzoyl)-benzofuran 6-yl]-oxalamic acid isopropyl ester of the formula

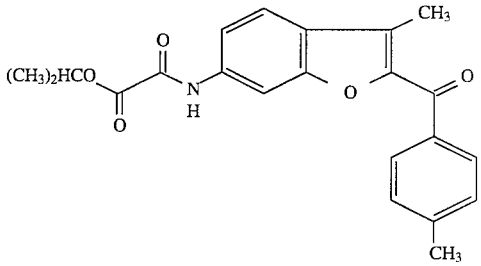

or a salt thereof.

7. A compound according to claim 1 wherein such compound is 3-[6-(carboxycarbonylamino)-2-(pyridine-3-carbonyl)-benzofuran-3-yl]-propionic acid of the formula

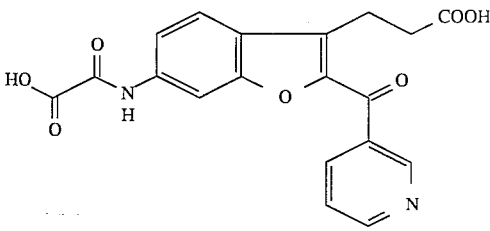

or a salt thereof.

8. A compound according to claim 1 wherein such compound is N-[3-methyl-2-(pyridine- 4-carbonyl)-benzofuran-5-yl]-oxalamic acid ethyl ester of the formula

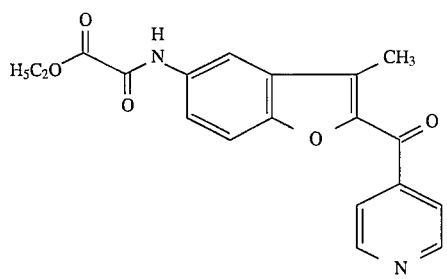

or a salt thereof.

9. A compound according to claim 1 wherein such compound is N-[3-ethyl-2-(4-methyl-benzoyl)-benzofuran-5-yl]-oxalamic acid of the formula

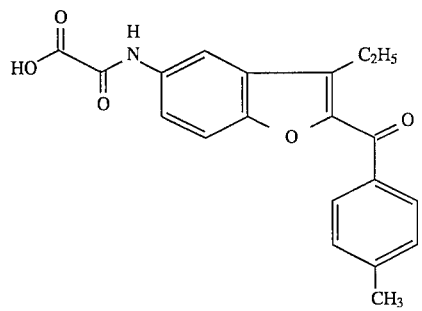

or a salt thereof.

10. An anti-inflammatory composition comprising an amount effective therefor of a compound or salt according to claim 1 and a pharmacologically acceptable diluent.

11. A method of decreasing inflammation in a patient in need thereof which comprises administering to such patient an amount effective therefor of a compound or salt according to claim 1.

12. The method according to claim 11, wherein such compound is

N-[3-methyl-2-(4-methyl-benzoyl)-benzofuran-6-yl]-oxalamic acid ethyl ester,

N-[2-(biphenyl-4-carbonyl)-3-methyl-benxofuran-6-yl]-oxalamic acid,

N-[3-methyl-2-(4-methyl-benzoyl)-benzofuran 6-yl]-oxalamic acid isopropyl ester, 3-[6-(carboxycarbonylamino)-2-(pyridine-3-carbonyl)-benzofuran-3-yl]-propionic acid, N-[3-methyl-2-pyridine-4-carbonyl)-benzofuran-5-yl]-oxalamic acid ethyl ester, or N-[3-ethyl-2-(4-methyl-benzoyl)-benzofuran-5-y]-oxalamic acid or salt thereof.

* * * * *

UNITED STATES PATENT AND TRADEMARK OFFICE
CERTIFICATE OF CORRECTION

PATENT NO. : 5,565,488
DATED : October 15, 1996
INVENTOR(S) : Braunlich, et al.

It is certified that error appears in the above-indentified patent and that said Letters Patent is hereby corrected as shown below:

Title Page    OTHER PUBLICATIONS: Insert -- Chemical Abstracts, Vol. 77, No. 23, Abstract No. 151884g, (1972) --

Col. 105, line 43    Before " denotes " insert -- a --

Signed and Sealed this

Twenty-seventh Day of May, 1997

Attest:

BRUCE LEHMAN

Attesting Officer    Commissioner of Patents and Trademarks